United States Patent
Perez-Camargo et al.

(10) Patent No.: US 10,463,023 B2
(45) Date of Patent: Nov. 5, 2019

(54) METHODS AND APPARATUSES TO USE DURATION AND/OR FREQUENCY DATA FROM URINE AND/OR FECAL PET ELIMINATION BEHAVIORS

(71) Applicant: NESTEC SA, Vevey (CH)

(72) Inventors: Gerardo Perez-Camargo, House Springs, MO (US); Francois Martin, St. Joseph, MO (US); Ragen Trudelle-Schwarz McGowan, St. Joseph, MO (US)

(73) Assignee: SOCIÉTÉ DES PRODUITS NESTLÉ S.A., Vevey (CH)

( * ) Notice: Subject to any disclaimer, the term of this patent is extended or adjusted under 35 U.S.C. 154(b) by 910 days.

(21) Appl. No.: 15/066,538

(22) Filed: Mar. 10, 2016

(65) Prior Publication Data
US 2016/0262356 A1    Sep. 15, 2016

Related U.S. Application Data

(60) Provisional application No. 62/132,562, filed on Mar. 13, 2015.

(51) Int. Cl.
*A01K 29/00* (2006.01)
*A01K 1/01* (2006.01)
(Continued)

(52) U.S. Cl.
CPC .......... *A01K 29/005* (2013.01); *A01K 1/0107* (2013.01); *A01K 1/0152* (2013.01);
(Continued)

(58) Field of Classification Search
CPC .. A01K 1/0107; A01K 1/0047; A01K 1/0114; A01K 1/035; A01K 29/005
(Continued)

(56) References Cited

U.S. PATENT DOCUMENTS

| 5,662,066 A | * | 9/1997 | Reitz | A01K 1/0114 |
| | | | | 119/163 |
| 5,755,181 A | * | 5/1998 | Petkovski | A01K 1/0107 |
| | | | | 119/163 |

(Continued)

FOREIGN PATENT DOCUMENTS

EP        1625788      2/2006

OTHER PUBLICATIONS

Bakeman R., Gottman J. M. Observing Interactions: An Introduction to Sequential Analysis, 2nd Edition, 1997, p. 56-68 Cambridge University Press: Cambridge.

(Continued)

*Primary Examiner* — Yvonne R Abbott-Lewis

(57) ABSTRACT

The present disclosure provides a method for evaluating the appeal of a litter or the litter box environment to a cat and also provides a behavioral diagnostic method for assessing risk of urinary health issues. The methods involve the use of the duration of the elimination sequence to diagnose if the cat has a healthy (enriched environment) or unhealthy (standard environment) elimination behavior. The duration can be measured by an apparatus that determines the time of residence of an animal in a litter pan (i.e., the difference between time of entrance and time of exit from the pan). The apparatus can determine the time of residence of the animal in the litter pan using one or more of a motion detection device attached to the litter pan, an accelerometer attached to the litter pan, or a weight scale balance under the litter pan.

4 Claims, 8 Drawing Sheets

(51) Int. Cl.
*A01K 1/015* (2006.01)
*A61B 5/20* (2006.01)
*A61B 5/00* (2006.01)
*G16H 40/63* (2018.01)
*G16H 50/20* (2018.01)

(52) U.S. Cl.
CPC ............ *A61B 5/207* (2013.01); *A61B 5/4255* (2013.01); *A61B 5/7275* (2013.01); *G16H 40/63* (2018.01); *G16H 50/20* (2018.01); *A61B 2503/40* (2013.01); *A61B 2562/0204* (2013.01); *A61B 2562/0219* (2013.01)

(58) Field of Classification Search
USPC .................................. 119/165, 500, 163, 166
See application file for complete search history.

(56) References Cited

U.S. PATENT DOCUMENTS

| | | | | |
|---|---|---|---|---|
| 5,778,822 | A * | 7/1998 | Giffin | A01K 1/0047 119/165 |
| 6,041,737 | A * | 3/2000 | Hennigan | A01K 1/0107 119/161 |
| 6,082,302 | A * | 7/2000 | Thaler | A01K 1/0114 119/161 |
| 6,202,595 | B1 * | 3/2001 | Atcravi | A01K 1/0114 119/165 |
| 6,998,980 | B2 * | 2/2006 | Ingley, III | A01K 1/031 119/421 |
| 7,905,201 | B2 * | 3/2011 | Greene | A01K 1/011 119/421 |
| 8,297,230 | B2 * | 10/2012 | Ferrer | A01K 1/0047 119/165 |
| 2007/0288249 | A1 * | 12/2007 | Rowe | A01K 1/0023 705/7.11 |
| 2010/0218733 | A1 * | 9/2010 | Jordan | A01K 15/02 119/720 |
| 2012/0299731 | A1 * | 11/2012 | Triener | G01G 17/08 340/573.1 |

OTHER PUBLICATIONS

Beaver, B. V. Feline Behavior: A Guide for Veterinarians. 2003 p. 247 Saint Louis: Saunders.
Cafazzo S. and Natoli E. The social function of tail up in the domestic cat (*Felis silvestris catus*). Behavioural Processes. vol. 80 No. 1, 2009 pp. 60-66.
Cottam N. and Dodman N. H. Effect of an odor eliminator on feline litter box behavior. Journal of Feline Medicine and Surgery 2007 pp. 44-50.
Fogle B. The Cat's Mind, Understanding Your Cat's Behavior, 1992 pp. 50-66.
Hartwell S. Cat communication—Body language. 2009 www.messybeast.com/cat_talk2.htm.
Houpt K. A. Personal communication. Published in Beaver, B. V. (2003). Feline Behavior: A Guide for Veterinarians. Saunders: Saint Louis. pp. 249-250 and 268.
Horwitz D. Behavioral and environmental factors associated with elimination behavior problems in cats: A retrospective study. Applied Animal Behaviour Science. 52, 1997 pp. 129-137.
Jackson W. B. Food habits of Baltimore, Maryland, cats in relation to rat populations. Journal of Mammalogy, vol. 32 No. 4, 1951 pp. 458-461.
Kiley-Worthington M. Tail movements of ungulates, canids, and felids with particular reference to to their causation and functional displays. Behaviour, 1975 pp. 69-115.
Lane D. R., Cooper B. C. Veterinary Nursing. 3rd Edition Butterworth-Heinemann Ltd, Massachusetts. Jul. 18, 2017, pp. 2-3.
Liberg O. Spacing patterns in a population of rural free roaming domestic cats, Nordic Society Oikos, vol. 35 No. 3, 1980 pp. 336-349.
Marder, Amy Managing behavioral problems in puppies and kittens. Friskies PetCare Small Animal Behavior. 1997 pp. 15-24.
Panaman R. Behaviour and ecology of free-ranging female farm cats (*Felis catus* L.). 1981, pp. 56, 59-73., Z. Tierpsychol.
Salman M. D., and Hutchison J., and Ruch-Gallie R. Behavioral reasons for relinquishment of dogs and cats to 12 shelters. Journal of Applied Animal Welfare Science, Jun. 4, 2010, pp. 93-106.
Spooner S.K. Determination of the Normal ethogram of Feline Urinary Behavior. Doctorate Thesis. 1990 pp. 1-149.
Sung W. The elimination behavior patterns of domestic cats (*Felis catus*) with and without elimination problems. 2001 pp. 1-34.
Sung W., and Crowell-Davis S. L. The elimination behavior patterns of domestic cats (*Felis catus*) with and without elimination problems. American Journal of Veterinary Research, vol. 67 No. 9, 2006 pp. 1500-1504.
UK Cat Behaviour Working Group an ethogram for behavioural studies of the domestic cat (*Felis silvestris catus* L.). Universities Federation for Animal Welfare, 1995 pp. 1-32.
Voith V. L. Attachment of people to companion animals. The Veterinary Clinics of North America, vol. 15, No. 2, Mar. 1985, pp. 289-295.
International Search Report for PCT Application No. PCT/IB16/051378 dated Aug. 9, 2016.

\* cited by examiner

METHODS AND APPARATUSES TO USE DURATION AND/OR FREQUENCY DATA FROM URINE AND/OR FECAL PET ELIMINATION BEHAVIORS

CROSS REFERENCE TO RELATED APPLICATIONS

This application claims priority to U.S. Provisional Application No. 62/132,562 filed Mar. 13, 2015, the disclosure of which is incorporated herein by this reference.

BACKGROUND

The present disclosure relates generally to apparatuses and methods that use the duration and/or the frequency of animal urination and/or defecation ("elimination"), for example to evaluate the appeal of cat litter. More specifically, the present disclosure is directed to apparatuses and methods that use the duration and/or the frequency of the elimination sequence to diagnose if an animal has a healthy (enriched environment) or unhealthy (standard environment) elimination behavior.

Litter boxes are used by cats for elimination of urine and fecal matter. A litter box contains a layer of cat litter that receives the urine and fecal matter. The cat litter is granular and absorbent to facilitate formation of clumps after the urine and fecal matter is deposited in the cat litter. The clumps are typically sifted from the litter box using a litter scoop and then discarded.

Out of box elimination (also known as inappropriate elimination or house soiling) is the most common complaint of cat owners either seeking the help of professional behaviorists (Voith, 1985) or surrendering their cats to a shelter (Salman, Hutchison & Ruch-Gallie, 2000). Eliminating outside the box is the main behavioral reason for cats to be relinquished to shelters, and these cats have poor chances to be rehomed and often end up being put down.

Most published studies on cat elimination behavior have approached the topic from the context of diagnosing and treating out of box eliminations. While many professors, behaviorists and veterinarians have studied factors that may cause cats to reject their litter box, there has been little effort to distinguish positive from negative in-box experiences. Little is known about normal domestic cat elimination behavior.

There is currently no easy way to assess if the cat is using the litter box properly. Cats usually eliminate while the owner is not looking and frustration behaviors cannot be observed. Moreover, pet owners lack animal behavioural knowledge to identify if the cat has an issue with the litter.

Some previous studies (N. Cottam and N. Dodman, 2007) used videotaping of the cat in the litter box to evaluate expression of positive and negative elimination behaviors. The drawbacks of this approach are: (i) the behavior of the cats can be affected by the presence of a motion detection camera, and (ii) the video footage needs to be scored by a qualified and experienced behaviourist.

SUMMARY

An aspect of the present disclosure is a method for evaluating the appeal of a litter or the litter box environment to a cat. Another aspect of the present disclosure is a behavioral diagnostic method for assessing risk of urinary health issues. The methods involve the use of the duration of the elimination sequence to diagnose if the cat has a healthy (enriched environment) or unhealthy (standard environment) elimination behavior. During a behavior research project, the present inventors discovered a surprising relationship between cat appeal of the litter box and shorter elimination sequences. The duration can be measured by an apparatus that determines the time of residence of an animal in a litter pan (i.e., the difference between time of entrance into the pan and time of exit from the pan). The apparatus can determine the time of residence of the animal in the litter pan using one or more of a motion detection device attached to the litter pan, an accelerometer attached to the litter pan, or a weighing scale under the litter pan.

Specifically, research by the inventors showed that duration of the elimination is a key indicator of whether the cat has a good experience (150-250 seconds) or a bad elimination pattern (lasting over 300 seconds). In addition, cats disliking the litter box held their urine and then urinated less often and for a longer duration, with their urine stream lasting on average 52 seconds (compared to 3.3 seconds when they liked the litter). When cats have a good experience they saw healthy elimination patterns, eliminating more frequently and for shorter time. When cats have bad elimination patterns, they wait longer between elimination events. These waiting periods are associated with (i) a disease risk: longer residence time of the urine in the bladder of the cat is a predisposing factor for the aggregation of solutes in urine and the formation of urinary crystals (struvite, oxalate) or stones, and (ii) a behavioral issue risk: cats that have a poor elimination behavior are more likely to eliminate out of their litter pan and soil the house.

Accordingly, in a general embodiment, the present disclosure provides a method comprising measuring a duration of each of a plurality of elimination sequences of an animal which uses a litter pan containing litter, and the measuring of the duration is performed using at least one detection device selected from the group consisting of a motion detection device, an accelerometer, and a weighing scale.

In an embodiment, the method comprises determining an average duration of the plurality of elimination sequences. The average duration can be compared to a predetermined threshold. The determining of the average duration of the plurality of elimination sequences can be performed at least partially by a processor which is part of an apparatus that comprises a housing; and the litter pan, the at least one detection device, and the processor can be at least partially contained in the housing or at least partially affixed to the housing.

In an embodiment, the measuring of the duration of each of the plurality of elimination sequences comprises the at least one detection device sending signals to a processor and the processor classifying one of the signals as a beginning of an elimination sequence and another one of the signals as an ending of the elimination sequence.

In an embodiment, the plurality of elimination sequences are elimination sequences that occur during a predetermined time period.

In an embodiment, the method does not include generating or recording photographs or video of the animal during the plurality of elimination sequences.

In another embodiment provided by the present disclosure, a method comprises: identifying elimination sequences of an animal which uses a litter pan containing litter, and the identifying is performed using at least one detection device selected from the group consisting of a motion detection device, an accelerometer, and a weighing scale; and determining a frequency of elimination based on the elimination sequences, and the determining is performed by a processor communicatively connected to the at least one detection device.

In an embodiment, the method comprises comparing the frequency of elimination to a predetermined threshold.

In an embodiment, the processor is part of an apparatus comprising a housing; and the litter pan, the at least one detection device, and the processor are at least partially contained in the housing or at least partially affixed to the housing.

In another embodiment, the present disclosure provides an apparatus comprising: a litter pan configured to hold litter; at least one detection device selected from the group consisting of a motion detection device, an accelerometer, and a weighing scale; a processor configured to receive signals from the at least one detection device and use the signals to identify elimination sequences of an animal using the litter pan; and a housing, wherein the litter pan, the at least one detection device, and the processor are at least partially contained in the housing or at least partially affixed to the housing.

In an embodiment, the processor is configured to determine an average duration of the elimination sequences.

In an embodiment, the processor is configured to determine a frequency of elimination over a predetermined time period.

In an embodiment, the apparatus does not include a device that generates or records photographs or video of the animal using the litter pan.

In an embodiment, the at least one detection device comprises a motion detection device connected to the litter pan.

In an embodiment, the at least one detection device comprises an accelerometer connected to the litter pan.

In an embodiment, the at least one detection device comprises a weighing scale connected to the litter pan.

In another embodiment, the present disclosure provides a method of determining litter appeal. The method comprises: identifying a plurality of elimination sequences of an animal which uses a litter pan containing litter, and the identifying is performed using at least one detection device selected from the group consisting of a motion detection device, an accelerometer, and a weighing scale; comparing to a threshold at least one of (i) an average duration of the plurality of elimination sequences or (ii) a frequency of elimination based on the plurality of elimination sequences; and classifying an appeal of the litter, the classifying based at least partially on the comparing.

In an embodiment, the method comprises packaging the litter in a container comprising indicia based at least partially on the comparing.

In another embodiment, the present disclosure provides a method of evaluating litter preference. The method comprises: placing a first type of litter in a litter pan; identifying a first plurality of elimination sequences of an animal which uses the litter pan containing the first type of litter, and the identifying of the first plurality of elimination sequences is performed using at least one detection device selected from the group consisting of a motion detection device, an accelerometer, and a weighing scale; placing a second type of litter in a litter pan; identifying a second plurality of elimination sequences of an animal which uses the litter pan containing the second litter, and the identifying of the second plurality of elimination sequences is performed using the at least one detection device; and comparing at least one of (i) an average duration of the first plurality of elimination sequences to an average duration of the second plurality of elimination sequences or (ii) a frequency of elimination based on the first plurality of elimination sequences to a frequency of elimination based on the second plurality of elimination sequences.

In another embodiment, the present disclosure provides a method of determining whether an animal is at risk of a urinary tract condition. The method comprises: identifying a plurality of elimination sequences of an animal, the identifying performed using at least one detection device selected from the group consisting of a motion detection device, an accelerometer, and a weighing scale; comparing to a threshold at least one of (i) an average duration of the plurality of elimination sequences or (ii) a frequency of elimination based on the plurality of elimination sequences; and identifying whether the animal is at risk of a urinary tract condition, the identifying based at least partially on the comparing.

In another embodiment, the present disclosure provides a method of determining whether an animal is at risk of outside the box elimination, the method comprising: identifying a plurality of elimination sequences of an animal which uses a litter pan containing litter, the identifying performed using at least one detection device selected from the group consisting of a motion detection device, an accelerometer, and a weighing scale; comparing to a threshold at least one of (i) an average duration of the plurality of elimination sequences or (ii) a frequency of elimination based on the plurality of elimination sequences; and identifying whether the animal is at risk of outside the box elimination, the identifying based at least partially on the comparing.

An advantage of the present disclosure is to use the duration of the cat elimination as the key indicator of the healthy use of the litter box and thereby make evaluation of the cat litter simpler, more accurate, and easier to measure relative to the known methods which typically employ behavioral analysis.

Another advantage of the present disclosure is to identify a type of cat litter having appeal for a domestic cat and thus increasing the probability that the owner will keep the cat and not relinquish the cat to shelter.

A further advantage of the present disclosure is to compare the cat appeal of different litter products and thus develop better products.

Still another advantage of the present disclosure is to allow substantiation of claims regarding the appeal of cat litter, such as "this litter is preferred by cats" and "this litter is designed to please a cat's natural elimination behavioral needs."

Yet another advantage of the present disclosure is to use the duration of elimination in an in-home veterinary diagnostic tool to identify cats at risk of developing lower urinary tract health issues.

Another advantage of the present disclosure is to use the duration of elimination in an in-home behavioral diagnostic tool to identify cats that have a poor environment causing stress and increased likelihood of eliminating around the house but out of their litter pan.

A further advantage of the present disclosure is to provide an apparatus that can be set up at any location.

Additional features and advantages are described herein and will be apparent from the following Detailed Description and the Figures.

DETAILED DESCRIPTION

As used in this disclosure and the appended claims, the singular forms "a," "an" and "the" include plural referents unless the context clearly dictates otherwise. Thus, for example, reference to "a processor" or "the processor" includes two or more processors.

The words "comprise," "comprises" and "comprising" are to be interpreted inclusively rather than exclusively. Likewise, the terms "include," "including" and "or" should all be construed to be inclusive, unless such a construction is clearly prohibited from the context. However, the devices disclosed herein may lack any element that is not specifically disclosed. Thus, a disclosure of an embodiment using the term "comprising" includes a disclosure of embodiments "consisting essentially of" and "consisting of" the components identified.

The term "and/or" used in the context of "X and/or Y" should be interpreted as "X," or "Y," or "X and Y." Where used herein, the term "example," particularly when followed by a listing of terms, is merely exemplary and illustrative, and should not be deemed to be exclusive or comprehensive.

As used herein, "about" is understood to refer to numbers in a range of numerals, for example the range of −10% to +10% of the referenced number, preferably within −5% to +5% of the referenced number, more preferably within −1% to +1% of the referenced number, most preferably within −0.1% to +0.1% of the referenced number.

The terms "pet" and "animal" mean any animal which can use a litter box, such as a cat, a dog, a rat, a ferret, a hamster, a rabbit, an iguana, a pig or a bird. The pet can be any suitable animal, and the present disclosure is not limited to a specific pet animal. The term "companion animal" means a dog or a cat. The term "elimination" means urination and/or defecation by an animal. The term "elimination sequence" means the time period from when an animal enters a litter pan for elimination to when the animal exits the litter pan after elimination.

The methods and devices and other advances disclosed herein are not limited to particular methodologies, protocols, and reagents because, as the skilled artisan will appreciate, they may vary. Further, the terminology used herein is for the purpose of describing particular embodiments only and does not limit the scope of that which is disclosed or claimed.

Unless defined otherwise, all technical and scientific terms, terms of art, and acronyms used herein have the meanings commonly understood by one of ordinary skill in the art in the field(s) of the present disclosure or in the field(s) where the term is used. Although any compositions, methods, articles of manufacture, or other means or materials similar or equivalent to those described herein can be used, the preferred devices, methods, articles of manufacture, or other means or materials are described herein.

Figure 1:
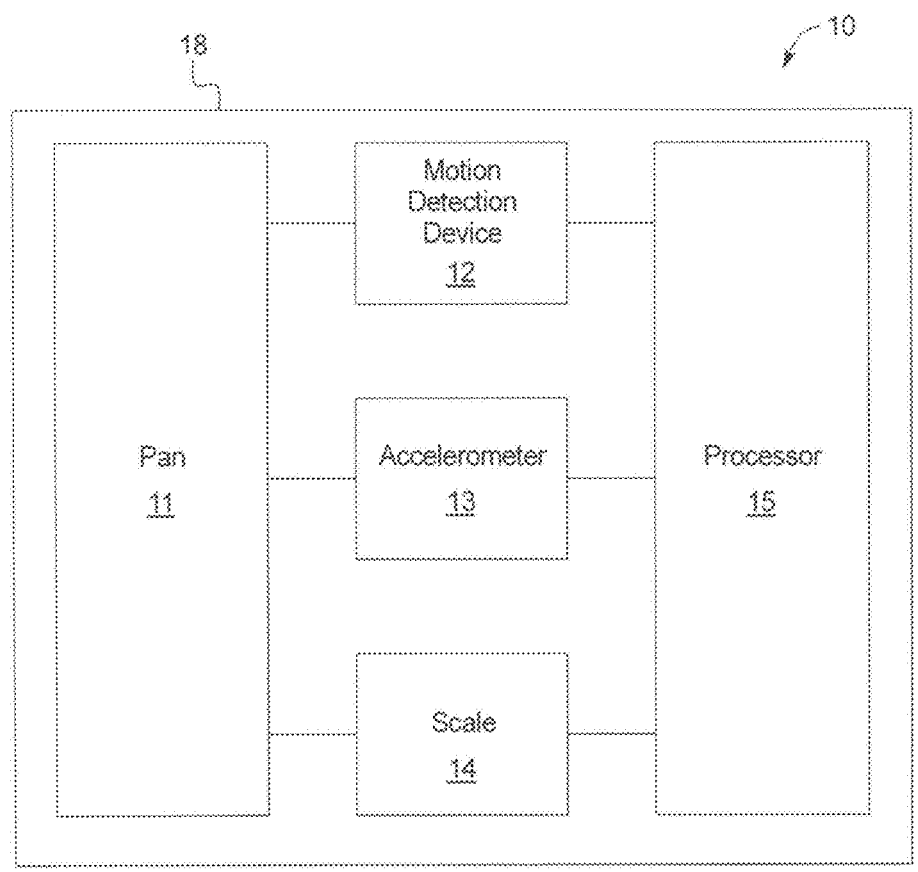
FIG. 1 shows a schematic diagram of an embodiment of an apparatus provided by the present disclosure.

FIG. 1 generally illustrates an embodiment of an apparatus 10 provided by the present disclosure. The apparatus 10 can measure the duration of elimination sequences as discussed in detail hereafter. The apparatus 10 comprises a housing 18 and a litter pan 11. The litter pan 11 can have any form and any size that are suitable for containing litter. Preferably, the litter pan 11 comprises a bottom wall and one of more side walls that define an interior in which the litter can be held.

The apparatus 10 further comprises at least detection device selected from the group consisting of a motion detection device 12 connected to the litter pan 11, an accelerometer 13 connected to the litter pan 11, and a weighing scale 14 connected to the litter pan 11. One, two, or all three of these detection devices can be present in the apparatus 10 in various embodiments. In a preferred embodiment, these one or more detection devices are sufficient, and the apparatus 10 does not include a camera or any other device which generates photographs or video of the animal using the litter pan and is not connected to such a device.

The motion detection device 12, if present in the apparatus 10, can be (i) any device capable of detecting a change in position of the litter pan 11 relative to the housing 18 and/or another component of the apparatus 10 and/or (ii) any device capable of detecting motion in the area directly above the litter pan 11. For example, the motion detection device 12 can perform mechanical motion detection, electronic motion detection, or both.

In an embodiment, the motion detection device 12 is a mechanical motion detection device, such as a switch that moves between an activated position and an inactivated position. In an embodiment, the motion detection device 12 is an electronic motion detection device, such as a sensor that uses one or more of infrared light (e.g., passive and active sensors), optics (e.g. video and camera systems), radio frequency energy (e.g., radar, microwave and tomographic motion detection), sound (e.g. microphones and acoustic sensors), vibration (e.g., triboelectric, seismic and inertia-switch sensors), and magnetism (e.g. magnetic sensors and magnetometers). In some embodiments, the motion detection device 12 uses both mechanical and electronic motion detection. Regardless, the apparatus 10 is not limited to a specific embodiment of the motion detection device 12.

The accelerometer 13, if present in the apparatus 10, can be any device capable of detecting physical acceleration experienced by the litter pan 11. For example, the accelerometer 13 can be a piezoelectric device, a piezoresistive device, and/or a capacitive device.

The weighing scale 14, if present in the apparatus 10, can be any device capable of determining the weight or mass of the litter pan 11 with contents therein (e.g., litter and periodically an animal). The weighing scale 14 can be an electronic scale and/or a mechanical scale, such as a balance scale. In an embodiment, the weighing scale 14 is positioned under the litter pan 11.

A processor 15 can be connected to the at least one detection device (i.e., connected to one or more of the motion detection device 12, the accelerometer 13, or the weighing scale 14). Preferably the apparatus 10 is a single unit such that the litter pan 11, the processor 15, and the at least one detection device are at least partially contained in the housing 18 and/or affixed on the housing 18. For example, one or more of the litter pan 11, the processor 15, or the at least one detection device can be connected to the housing 18 such that tools are required for removal and reattachment. As another example, one or more of the litter pan 11, the processor 15, or the at least one detection device can be reversibly connected to the housing 18 so that a user can perform removal and reattachment by hand without tools.

The processor 15 can use signals, such as measurements, from the motion detection device 12, the accelerometer 13 and/or the scale 14 to determine the duration of the elimination sequence of an animal using the litter pan 11. Depending on the specific type of detection device present in the apparatus 10, the processor 15 can be configured to use one or more of detection of motion of the litter pan 11, detection of motion directly above the litter pan 11, physical acceleration experienced by the litter pan 11, or increased weight of the litter pan 11 to determine the duration of the elimination sequence of the animal using the litter pan 11. For example, a signal from the one or more detection devices can be characterized by the processor 15 as the beginning of an elimination sequence, another signal from the one or more detection devices can be characterized by the processor 15 as the ending of the elimination sequence. The processor can determine the amount of time between the beginning and the end of the elimination sequence.

The processor 15 can record the duration of the elimination sequence, preferably in association with a time, more preferably with both a time and a date. The processor 15 can record the duration, the time, and the date for each of a plurality of elimination sequences and use this information to determine an average duration of elimination and/or a frequency of elimination. This information can be recorded over a predetermined time period.

In an embodiment, the apparatus 10 can comprise an output component (not shown) which can be integral with the housing 18, and the processor 15 can use the output component to display the average duration of elimination and/or the frequency of elimination. Alternatively or additionally, the apparatus 10 can transmit the average duration of elimination and/or the frequency of elimination to another device, such as a desktop computer, a laptop computer, or a mobile telephone, for example using a wired or wireless communication connection. In an embodiment, the other device can perform at least a portion of the calculations that determine average duration of elimination and/or the frequency of elimination.

In an embodiment, the processor 15 can compare the average duration of elimination and/or the frequency of elimination to a respective predetermined threshold to determine the satisfaction of the animal with respect to the litter in the litter pan 11. In an embodiment, the processor 15 can compare the average duration of elimination and/or the frequency of elimination to a respective predetermined threshold to determine if the animal is at risk of urinary health issues, such as feline lower urinary tract disease. For example, in the behavioral study using cats that is detailed herein, the present inventors found that duration of the elimination is a key indicator of whether the cat has a good experience (150-250 seconds) or a bad elimination pattern (lasting over 300 seconds). In addition, cats disliking the litter box held their urine and then urinated less often and for a longer duration, with their urine stream lasting on average 52 seconds (compared to 3.3 seconds when they liked the litter).

The processor 15 can use the output component and/or the other device to display a message that indicates whether the average duration of elimination and/or the frequency of elimination exceed a corresponding predetermined threshold or not.

In a particularly preferred embodiment, the apparatus 10 determines the duration of the elimination sequence automatically without any user input indicating that an elimination sequence is occurring, for example without any user input indicating that an elimination sequence has initiated and without any user input indicating that an elimination sequence has ended.

Another aspect of the present disclosure is a method of evaluating litter appeal. The method can use the apparatus 10 and/or another apparatus. The method can comprise placing a first type of litter in a litter pan, measuring the duration of each of a first plurality of elimination sequences of an animal using the litter pan containing the first type of litter, and determining the average duration of the first plurality of elimination sequences. The animal is preferably a companion animal and more preferably a cat. The first plurality of elimination sequences can be the elimination sequences that occur during a first predetermined time period.

The measuring of the duration of each of the first plurality of elimination sequences preferably uses at least one detection device selected from the group consisting of a motion detection device, an accelerometer connected to the litter pan, and a weighing scale connected to the litter pan. The measuring of the duration of each of the first plurality of elimination sequences preferably does not include recording video of the animal using the litter pan and preferably does not include observing the animal using the litter pan either in-person or by video.

In an embodiment, the method further comprises comparing the average duration of the first plurality of elimination sequences to a predetermined duration threshold, for example 250 seconds or 300 seconds, to evaluate the appeal of the litter to the animal. Preferably the duration of the elimination sequence is determined automatically without any user input indicating that an elimination sequence is occurring, for example without any user input indicating that an elimination sequence has initiated and without any user input indicating that an elimination sequence has ended.

In an embodiment, the duration of each of the first plurality of elimination sequences is associated with a time and preferably also with a date, and the time and the date are used to determine the frequency of elimination. In this embodiment, the evaluating of the appeal of the litter to the animal can comprise comparing the frequency of elimination to a predetermined frequency threshold.

In an embodiment, the method further comprises placing a second type of litter in the litter pan, measuring the duration of each of a second plurality of elimination sequences of the animal using the litter pan containing the second type of litter, determining the average duration of the second plurality of elimination sequences, and comparing the average duration of the first plurality of elimination sequences to the average duration of the second plurality of elimination sequences. The second plurality of elimination sequences are preferably the elimination sequences that occur during a second predetermined time period that is about the same length as the first predetermined time period and with the same and similar environmental conditions. This embodiment of the method can further comprise comparing the average frequency of the first plurality of elimination sequences to the average frequency of the second plurality of elimination sequences.

The type of cat litter which had shorter duration eliminations and/or more frequent eliminations can be identified as preferable relative to the other type of cat litter. For example, the type of cat litter which had shorter duration eliminations and/or more frequent eliminations can be packaged in a suitable container that indicates that this type of litter is designed to please a cat's natural elimination behavioral needs.

Yet another aspect of the present disclosure is a method of assessing whether an animal is at risk of a urinary health condition, for example at risk of aggregation of solutes in urine and formation of urinary crystals (struvite, oxalate) or stones from the aggregation. The method can use the apparatus 10 and/or another apparatus. The method can comprise measuring the duration of each of a plurality of elimination sequences of an animal using a litter pan, determining the average duration of the plurality of elimination sequences, and comparing the average duration of the plurality of elimination sequences to a predetermined duration threshold. The animal is preferably a companion animal and more preferably a cat.

The measuring of the duration of each of the plurality of elimination sequences preferably uses at least one detection device selected from the group consisting of a motion detection device, an accelerometer connected to the litter pan, and a weighing scale connected to the litter pan. The measuring of the duration of each of the first plurality of elimination sequences preferably does not include recording video of the animal using the litter pan and preferably does not include observing the animal using the litter pan either in-person or by video. Preferably the duration of the elimination sequence is determined automatically without any user input indicating that an elimination sequence is occurring, for example without any user input indicating that an elimination sequence has initiated and without any user input indicating that an elimination sequence has ended.

The method preferably comprises identifying the animal as at risk of a urinary health condition if the average duration exceeds the predetermined duration threshold or identifying the animal as not at risk of a urinary health condition if the average duration is below the predetermined duration threshold.

In an embodiment, the duration of each of the plurality of elimination sequences is associated with a time and preferably also with a date, and the time and the date are used to determine the frequency of elimination. In this embodiment, the method preferably comprises comparing the frequency of elimination to a predetermined frequency threshold, and the identifying of the animal as at risk of a urinary health condition or not is based at least partially on the comparison of the frequency of elimination to the predetermined frequency threshold.

A further aspect of the present disclosure is a method of assessing whether an animal has poor elimination behavior, for example is at risk of out of box eliminations. The method can use the apparatus 10 and/or another apparatus. The method can comprise measuring the duration of each of a plurality of elimination sequences of an animal using a litter pan, determining the average duration of the plurality of elimination sequences, and comparing the average duration of the plurality of elimination sequences to a predetermined duration threshold. The animal is preferably a companion animal and more preferably a cat.

The measuring of the duration of each of the plurality of elimination sequences preferably uses at least one detection device selected from the group consisting of a motion detection device, an accelerometer connected to the litter pan, and a weighing scale connected to the litter pan. The measuring of the duration of each of the first plurality of elimination sequences preferably does not include recording video of the animal using the litter pan and preferably does not include observing the animal using the litter pan either in-person or by video. Preferably the duration of the elimination sequence is determined automatically without any user input indicating that an elimination sequence is occurring, for example without any user input indicating that an elimination sequence has initiated and without any user input indicating that an elimination sequence has ended.

The method preferably comprises identifying the animal as having poor elimination behavior if the average duration exceeds the predetermined duration threshold or identifying the animal as not having poor elimination behavior if the average duration is below the predetermined duration threshold.

In an embodiment, the duration of each of the plurality of elimination sequences is associated with a time and preferably also with a date, and the time and the date are used to determine the frequency of elimination. In this embodiment, the method preferably comprises comparing the frequency of elimination to a predetermined frequency threshold, and the identifying whether the animal has poor elimination behavior or not is based at least partially on the comparison of the frequency of elimination to the predetermined frequency threshold.

EXAMPLE

By way of example and not limitation, the following non-limiting behavioral study is illustrative of the concept of using the duration of the cat elimination sequence to evaluate the appeal of cat litter.

Observation Methods

The elimination behavior of twelve cats was observed (six male and six female). The cats ranged in age from one to five years. All cats were born and raised at a cattery in Saint Joseph, Mo. They were domestic short hairs and had a variety of coat patterns and colors including: tabby, torbi, calico, gray, black, black and white, and orange and white.

Eleven of the 12 cats were fed 75 g of ProPlan® daily. One cat was fed 75 g of Fancy Feast® dry mixed with a can of Fancy Feast® Gourmet. Fresh water was provided ad libitum to all cats daily.

The acclimation phase for the Enriched ("Positive") Environment began at 0800 hr on behavioral study day 1. Cats were placed individually in a large room (12×14') with elevated resting boards, toys, and a sandbox sized (35.5× 35.5×6.5") stainless steel litter box filled and maintained to at least 2 inches in depth with a loose sandy clay scooping litter (clumping litter).

The ethogram development phase for the Enriched ("Positive") Environment began at 0800 hr on behavioral study day 5 in the same room and with the same materials as in the acclimation phase. Cats were video-recorded with Mangold's VideoSyncPro software. The cat's behavior in and around the litter box was recorded for four consecutive days using four wireless video cameras.

For the ethogram development phase for the Standard Collection ("Frustrating") Environment, the litter box in the Enriched Environment was scooped twice daily (once between 0800-0900 hr and once again between 1500-1600 hr), and Standard Collection Environment litter boxes were replaced when excreta was present. Extra litter in the Enriched Environment and extra beads in Standard Collection Environment were added as needed, in order to keep a constant fill level over time. At the time of litter box scooping or changing, the environment was spot cleaned to remove any out of box excreta, loose hair, or spilled food. The environments were completely sanitized between each cat.

Elimination events in the Enriched Environment and the Standard Collection Environment were coded and catalogued with Mangold's INTERACT 9 software.

Figure 2:
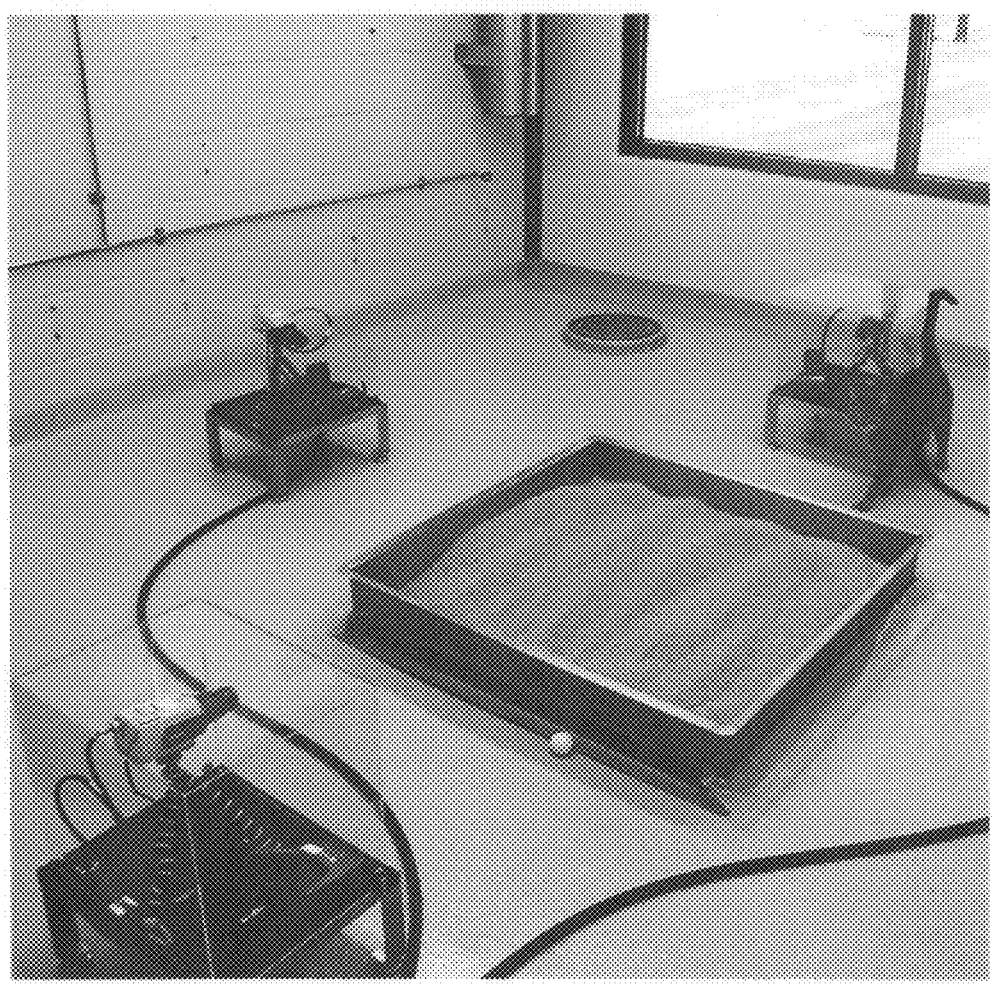
FIG. 2 is a photograph of the enriched ("positive") environment used in the behavioral study disclosed herein.

The Enriched Environment was presumed to offer a "positive" elimination experience for cats because it provided a large space, moisture absorbing fine grained litter, odor coverage, and offered the ability to conceal eliminations. The sandbox sized stainless steel litter box was maintained with at least two inches of scooping/clumping litter throughout the box. FIG. 2 is a photograph of the Enriched Environment.

The Standard Collection Environment was presumed to be a "frustrating" eliminating experience because it provided a reduced space, did not provide moisture absorbency or odor coverage, and did not offer the ability to conceal eliminations.

Behaviors Coded

The following section describes the behaviors coded in the ethogram. All behaviors were coded as frequencies with measurable durations, with the exception of shake movements and elimination site which were only coded as frequencies.

The following eight body postures are mutually exclusive.
Stand: Cat is positioned with 3-4 paws in contact with the ground with legs straight.
Sit: Cat rests fully on hind quarters with front legs straight, propping up chest and head.
Lying down: Cat is positioned with ventral or lateral side and legs in contact with the ground, paws folded or unfolded.
Stretch: Cat displays an extreme extension of the legs and either the front or back paws and away from the body. Also extreme arch back with legs fully extended.
Upright: Cat has both front paws pressed against a vertical surface.
Urination: Cat lowers hind legs and pelvis into a squatting position and urinates.
Defecation: Cat lowers hind legs and pelvis into a squatting position and defecates.
Incomplete elimination: Cat lowers hind legs and pelvis into a squatting position but does not eliminate.

The following two body movements are mutually exclusive.
Locomotion: Cat walks forward in a relatively straight line taking at least three steps. Front paws count steps.
Pivot: Cat rotates body 180° over a single focal point in a continuous motion. Interruptions greater than 1 second are considered a new behavior bout.
Interact with objects: Cat bats, moves, or plays with toy, litter box, litter/beads, or other object.
Vigilance: Cat suddenly becomes immobile, with body tense, eyes fixate away from litter environment. When cat focuses on multiple targets consecutively, scored as one event.
Eat/drink: Cat eats or drinks from food/water dishes.
Grooming: Cat cleans itself by licking its body or paws or cat scratches at self.

The following three shake movements are mutually exclusive. Due to the short duration only frequencies were coded.
Head shakes: Cat's head rotates to and fro in short, irregular, often jerky movements.
Body shakes: Cat's body rotates to and fro in short, irregular, often jerky movements.
Paw shakes: Cat shakes front or back paw/s in short, irregular, often jerky movements.
Ear wings: During elimination, cat's ears move out and to the side.
Flex: During elimination, cat's hips spasm in and out repeatedly.
Eye squint: During elimination, cat slowly narrows eyelids.
Over shoulder look: During elimination, cat looks back towards elimination spot. Not coded if it occurred at the very end of elimination.

The following four sniff/taste behaviors are mutually exclusive.
Sniff litter: Cat lowers head within two inches of the litter.
Sniff elimination: Cat lowers head within two inches of elimination site.
Sniff other: Cat extends or lowers head within two inches of a surface other than litter or elimination.
Taste litter: Cat places a small amount of litter in its mouth (may include elimination).
Balancing: Cat rests weight on sides of the litter box (minimal duration of 3 seconds to code this behavior).

The following five paw positions relative to the litter box are mutually exclusive.
0 paws: Cat outside of the litter box with no paws in the litter box.
1 paw: Cat has one paw within the litter box.
2 paws: Cat has two paws within the litter box.
3 paws: Cat has three paws within the litter box.
4 paws: Cat has all four paws within the litter box.

The following five tail positions are mutually exclusive.
Inverted U-tail: Cat's tail curled and held in the shape of an upside down "U".
Wagging: Cat's tail held out horizontally with the bottom half moving side to side.
Swish: Cat's tail held out horizontally and full tail is lashing from side to side.
Candy Cane: Cat's tail held out horizontally with the end of tail curled upwards.
Twitch: End of cat's tail makes brief motions but does not consistently move side to side.

Enriched Environment Box Zones

Figure 3:
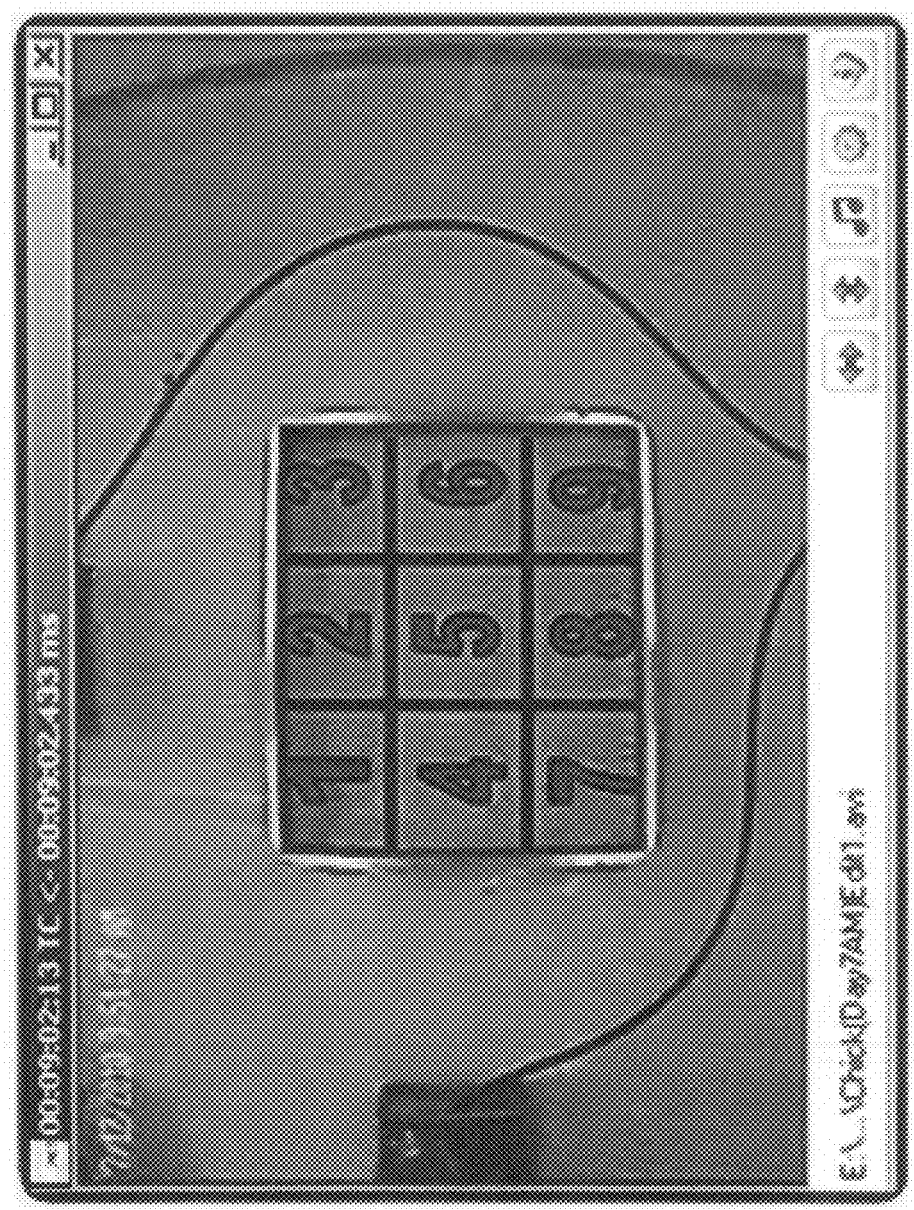
FIG. 3 shows the zones into which the litter box of the enriched ("positive") environment was divided.

Using the recordings from the camera mounted above the litter box, cat location in the litter box was coded by the location of the cat's nose. The location was recorded each time the nose changed zones. Duration was measured by time the nose was in each zone. The image in FIG. 3 depicts the nine (11.83×11.83") zones in the enriched environment. The nine litter box zones were mutually exclusive.

The elimination site was recorded as the box zone where the cat's hind-end was positioned while eliminating. The record was entered at the beginning of the elimination. This behavior had no duration.

Standard Collection Environment Box Zones

Using the recordings from the camera mounted above the litter box, the cat location in the litter box was coded by the location of the cat's nose. Location was recorded each time the nose changed zones. Duration was measured by time the nose was in each zone. The litter box in the standard environment was divided into four (8×4") zones, similar to how the litter box in the enriched environment was divided into nine zones. The four litter box zones in the standard environment were mutually exclusive.

The elimination site was recorded as the box zone where the cat's hind-end was positioned while eliminating. The record was entered at the beginning of the elimination. This behavior had no duration.

Other Information

Times of day that elimination occurred were recorded. In addition, the occurrence and location of out of box eliminations were recorded.

Data Analysis

The data was collected by two coders. Elimination events were defined as the cat's initial interaction with the litter box before elimination until the cat exited the litter box after elimination. All events included a time buffer of 10 seconds before initially interacting with the litter box and 10 seconds after exiting the litter box.

The elimination events were divided into three segments: pre-, during, and post-elimination. The 10-second buffer before elimination was included in the pre-elimination segment. The pre-elimination segment ended at the start of excretion. The during elimination segment included the time in which the cat was urinating or defecating. The post-elimination phase included the time from the completion of excretion until the end of the 10-second buffer after the cat exited the box.

For data collection/ethogram validation, one day (24 hrs) in the Enriched Environment and one day (24 hrs) in the Standard Collection Environment were coded for each cat. Within each environment, the day selected was based on (1) whether there was both a urine and fecal event that day and (2) how many events occurred that day, with preference given to days with more events. A total of 91 events were coded in data collection/ethogram validation. All four days in the Enriched Environment and all four days in the Standard Collection Environment were used to create a distribution depicting the time of day that events occurred.

Inter-Rater Reliability

Thirteen (14%) of the total 91 elimination events coded in data collection/ethogram validation were randomly selected to check the inter-rater reliability of our two coders. The average Cohen's Kappa for all behavior classes coded was greater than 85%, with the exception of "Eye squint" which was at 70% concordance. Above 75% concordance between coders is generally characterized as excellent (Bakeman & Gottman, 1997, p. 66). Table 1 below provides the mean kappa score for each mutually exclusive behavior category in the ethogram.

TABLE 1

| Behavior Category | Mean Kappa Score (%) |
| --- | --- |
| Body postures | 95 |
| Body movement | 88 |
| Interact with objects | 100 |
| Vigilance | 100 |
| Eat/drink | 100 |
| Grooming | 100 |
| Shake movements | 96 |
| Ear wings | 89 |
| Flex | 100 |
| Eye squint | 70 |
| Over shoulder Look | 86 |
| Sniff/taste behavior | 89 |
| Paw motions | 88 |
| Balancing | 100 |
| Paw positions | 96 |
| Tail position | 91 |
| Box zone | 85 |
| Elimination site | 100 |

Statistics

Table 2 below shows the breakdown of the events coded in data collection/ethogram validation. Descriptive statistics (measures of central tendency) provided in this report are means and standard errors. Inferential statistics (comparisons between behavior in the enriched and standard environment) were made using the Friedman Chi Squared test, as normality could not be assumed given the small sample size and uneven number of elimination events between cats. Alpha was set at $p=0.01$.

Figure 4:
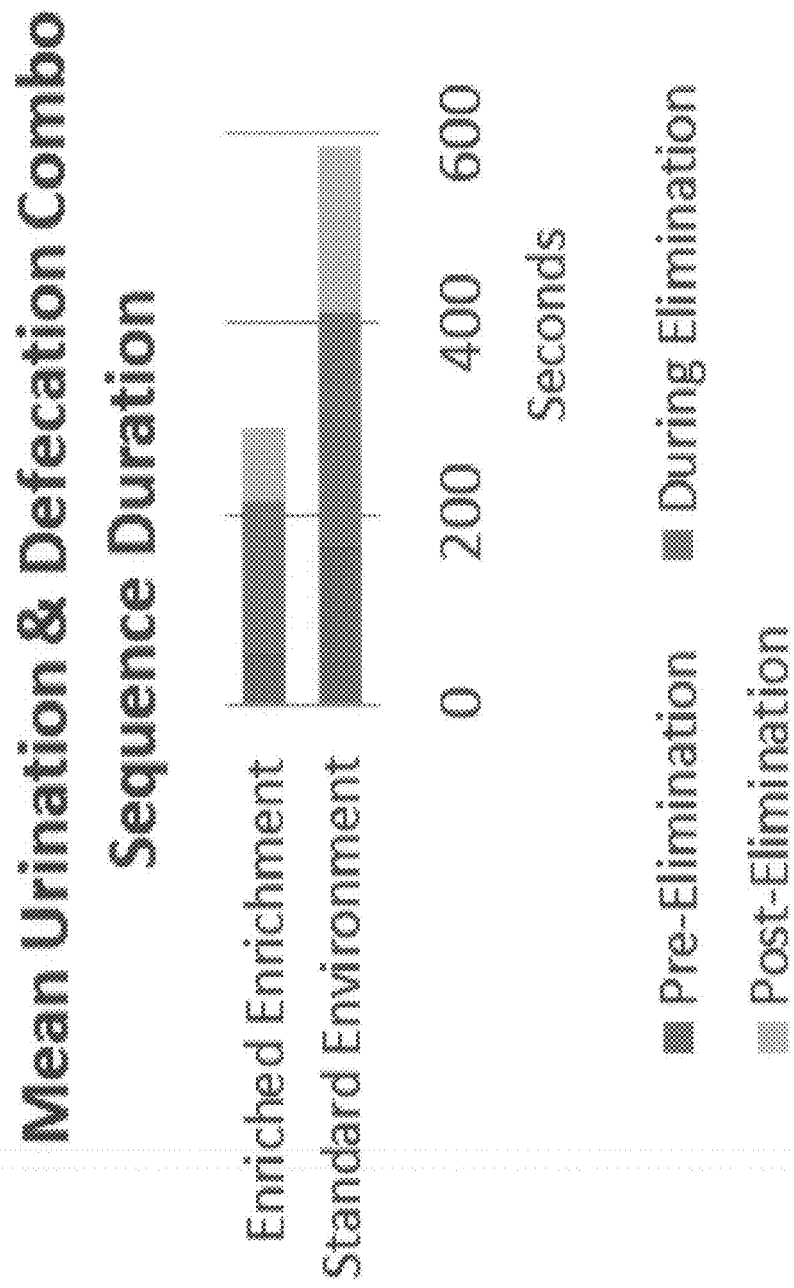
FIGS. 4-8 are graphs of results obtained in the behavioral study.

Urination & Defecation Combo Events were defined as eliminations in which less than one minute separated the excretion of urine and feces. These Combo events were made a separate category because which behaviors in the elimination sequence were associated with urination and which behaviors were associated with defecation could not be determined. FIG. 4 depicts the duration spent in the three elimination sequence segments (pre-, during, and post-elimination) for both environment types during the observed combo events.

However, as shown in Table 2, urination and defecation combo events were very infrequent. The number of events was too small to conduct inferential statistical tests. Therefore, the remainder of the study did not analyze combo elimination events.

TABLE 2

|  |  | Number of Events Coded |
| --- | --- | --- |
| Urinations | Enriched Environment | 40 |
|  | Standard Collection Environment | 18 |
| Defecations | Enriched Environment | 14 |
|  | Standard Collection Environment | 10 |
| Urination & Defecation Combo Events | Enriched Environment | 4 |
|  | Standard Collection Environment | 5 |

Urination Events

Figure 5:
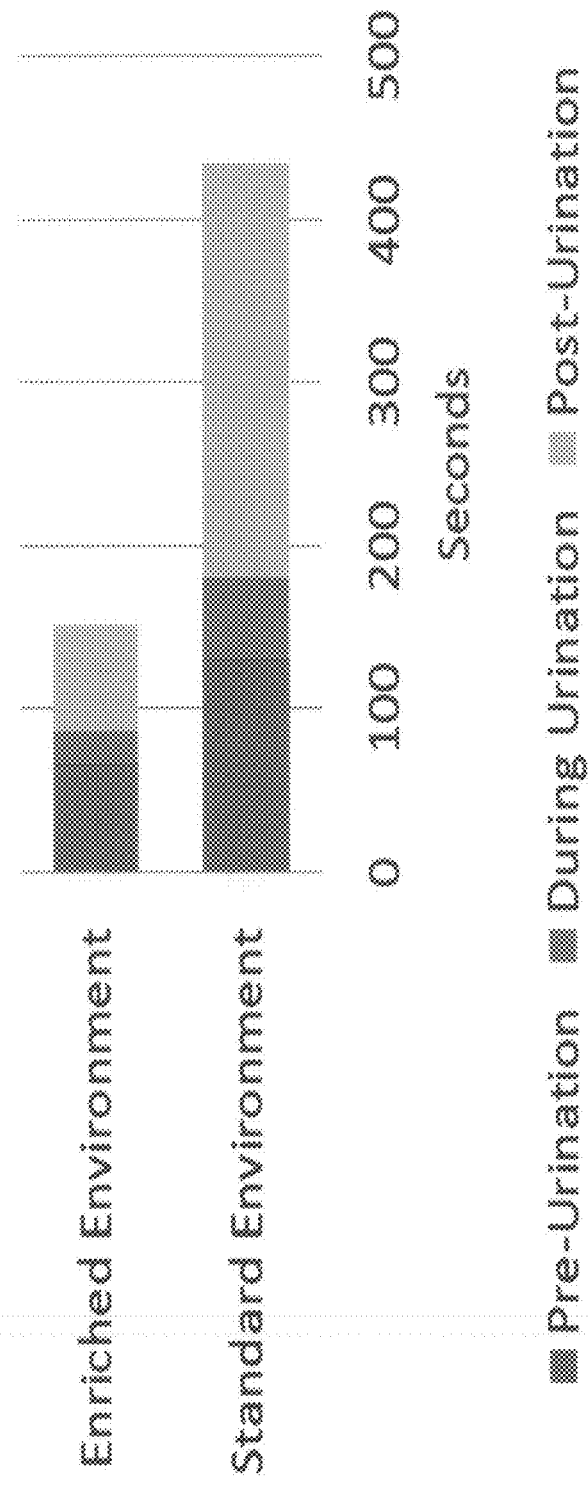

Table 2 above provides the number of cat urination events that were coded, and FIG. 5 depicts the duration spent in the three elimination sequence segments (pre-, during, and post-elimination) for both environment types during the observed urination events. In the Standard Collection Environment, the duration of the overall urination sequence, from pre- to post-urination, was longer than in the Enriched Environment, $X(1)=8.33$, $p=0.003$. In the Standard Collection Environment, the duration of the during urination segment ($X(1)=8.33$, $p=0.004$) and the post-urination segment ($X(1)=12.00$, $p=0.0005$) was longer than in the Enriched Environment.

Pre-Urination Segment

This section describes the pre-urination segment and compares the frequency and duration of the behaviors between the two environments.

Regarding body postures, the following postures were observed: stand, sit, lay, stretch, upright, and incomplete elimination. Table 3 below shows the frequency and duration of these postures. Body postures did not differ significantly between environments.

TABLE 3

|  | Enriched Environment | | Standard Collection Environment | |
| --- | --- | --- | --- | --- |
|  | M | SE | M | SE |
| Frequency of Postures Pre-Urination | | | | |
| Stand | 1.73 | 0.16 | 2.78 | 0.43 |
| Sit | 0.35 | 0.1 | 0.64 | 0.29 |
| Lay | 0.15 | 0.06 | 1.22 | 0.15 |
| Stretch | 0.18 | 0.06 | 0.11 | 0.88 |
| Upright | 0.03 | 0.03 | 0.06 | 0.06 |
| Incomplete elimination posture | 0.43 | 0.15 | 0.67 | 0.24 |
| Duration of Postures Pre-Urination (Sec) | | | | |
| Stand | 45.11 | 5.84 | 100.59 | 23.6 |
| Sit | 3.07 | 1.17 | 6.83 | 2.82 |
| Lay | 1.11 | 0.46 | 8.21 | 3.81 |
| Stretch | 0.49 | 0.17 | 0.54 | 0.41 |
| Upright | 0.05 | 0.54 | 0.33 | 0.33 |
| Incomplete elimination posture | 1.50 | 0.54 | 2.63 | 1.11 |

Table 4 below illustrates the frequency and durations of body movements. When in the Standard Collection Environment, cats pivoted more frequently, X(1)=8.33, p=0.004.

TABLE 4

|  | Enriched Environment | | Standard Collection Environment | |
| --- | --- | --- | --- | --- |
|  | M | SE | M | SE |
| Frequency of Body Movements Pre-Urination | | | | |
| Locomotion | 2.83 | 0.26 | 3.06 | 0.66 |
| Pivot | 0.60 | 0.16 | 4.72 | 0.84 |
| Duration of Body Movements Pre-Urination (Sec) | | | | |
| Locomotion | 14.5 | 1.25 | 13.24 | 3.05 |
| Pivot | 2.00 | 0.59 | 16.27 | 2.75 |

Table 5 below presents the frequency and duration of interactions with non-litter and non-elimination objects. No differences between environments were found.

TABLE 5

|  | Enriched Environment | | Standard Collection Environment | |
| --- | --- | --- | --- | --- |
|  | M | SE | M | SE |
| Interactions with Objects Pre-Urination | | | | |
| Frequency | 0.23 | 0.09 | 1.72 | 0.49 |
| Duration (Sec) | 0.92 | 0.45 | 16.02 | 7.64 |

Table 6 below shows the frequency and duration of vigilance. No differences between environments were found.

TABLE 6

|  | Enriched Environment | | Standard Collection Environment | |
| --- | --- | --- | --- | --- |
|  | M | SE | M | SE |
| Vigilance Pre-Urination | | | | |
| Frequency | 0.73 | 0.18 | 1.83 | 0.76 |
| Duration (Sec) | 2.90 | 0.78 | 9.38 | 4.79 |

Table 7 below displays the frequency and duration of eating/drinking. No differences between environments were found.

TABLE 7

|  | Enriched Environment | | Standard Collection Environment | |
| --- | --- | --- | --- | --- |
|  | M | SE | M | SE |
| Eating/Drinking Pre-Urination | | | | |
| Frequency | 0.03 | 0.03 | 0.39 | 0.16 |
| Duration (sec) | 0.10 | 0.10 | 1.93 | 0.88 |

Table 8 below shows the frequency and duration of grooming. No differences between environments were found.

TABLE 8

|  | Enriched Environment | | Standard Collection Environment | |
| --- | --- | --- | --- | --- |
|  | M | SE | M | SE |
| Grooming Pre-Urination | | | | |
| Frequency | 0.10 | 0.06 | 0.17 | 0.12 |
| Duration (sec) | 0.28 | 0.17 | 0.51 | 0.35 |

Regarding shake movements, Table 9 below presents the frequency of three types of shaking behavior. No differences between environments were found.

TABLE 9

|  | Enriched Environment | | Standard Collection Environment | |
| --- | --- | --- | --- | --- |
|  | M | SE | M | SE |
| Frequency of Shakes Pre-Urination | | | | |
| Head Shake | 0.43 | 0.12 | 0.56 | 0.34 |
| Body Shake | 0.13 | 0.05 | 0.11 | 0.08 |
| Paw Shake | 0.33 | 0.12 | 0.67 | 0.31 |

Table 10 below shows the frequency and duration for sniffing and tasting behaviors. In the Standard Collection Environment, cats sniffed other objects more often, X(1)=12.00, p=0.0005, and for an overall greater duration, X(1)=8.33, p=0.004.

TABLE 10

|  | Enriched Environment | | Standard Collection Environment | |
| --- | --- | --- | --- | --- |
|  | M | SE | M | SE |
| Frequency of Sniffing/Tasting Pre-Urination | | | | |
| Sniff Litter | 3.18 | 0.51 | 4.61 | 1.27 |
| Sniff Elimination | 0.45 | 0.16 | 0.89 | 0.62 |
| Sniff Other | 0.63 | 0.14 | 3.50 | 0.71 |
| Taste Litter | 0.20 | 0.15 | 0 | 0 |
| Duration of Sniffing/Tasting Pre-Urination (Sec) | | | | |
| Sniff Litter | 12.10 | 2.77 | 12.20 | 4.29 |
| Sniff Elimination | 1.25 | 0.44 | 2.48 | 1.94 |
| Sniff Other | 1.59 | 0.40 | 11.87 | 3.46 |
| Taste Litter | 1.31 | 0.87 | 0 | 0 |

Table 11 below gives the frequency and duration for paw motions. When housed in the Standard Collection Environment, cats pawed more frequently, X(1)=9.00, p=0.003, and for an overall greater duration, X(1)=9.00, p=0.003.

TABLE 11

|  | Enriched Environment | | Standard Collection Environment | |
| --- | --- | --- | --- | --- |
|  | M | SE | M | SE |
| Frequency of Paw Motions Pre-Urination | | | | |
| Pawing | 0 | 0 | 1.28 | 0.62 |
| Digging | 4.58 | 0.61 | 5.89 | 2.39 |
| Covering | 0.05 | 0.03 | 0 | 0 |
| Duration of Paw Motions Pre-Urination (Sec) | | | | |
| Pawing | 0 | 0 | 2.49 | 0.92 |
| Digging | 11.20 | 1.60 | 21.74 | 10.20 |
| Covering | 0.39 | 0.27 | 4.48 | 3.20 |

Regarding balancing, Table 12 below shows the frequency and duration that cats balanced on the litter box sides. No differences between environments were found.

TABLE 12

Balancing Pre-Urination

|  | Enriched Environment | | Standard Collection Environment | |
|---|---|---|---|---|
|  | M | SE | M | SE |
| Frequency | 0.28 | 0.08 | 0.11 | 0.76 |
| Duration (Sec) | 1.70 | 0.53 | 0.81 | 0.77 |

Regarding paw positions, Table 13 below provides the frequency and duration of the five paw positions relative to the litter box. In the Standard Collection Environment, cats more frequently put one paw in the box, $X(1)=7.36$, $p=0.01$.

TABLE 13

|  | Enriched Environment | | Standard Collection Environment | |
|---|---|---|---|---|
|  | M | SE | M | SE |
| Frequency of Paw Positions Pre-Urination | | | | |
| 0 paws in box | 1.07 | 0.04 | 2.94 | 0.62 |
| 1 paw in box | 1.15 | 0.10 | 4.67 | 1.12 |
| 2 paws in box | 1.15 | 0.08 | 4.33 | 0.99 |
| 3 paws in box | 1.10 | 0.08 | 3.78 | 0.79 |
| 4 paws in box | 1.05 | 0.05 | 2.33 | 0.48 |
| Duration of Paw Positions Pre-Urination (Sec) | | | | |
| 0 paws in box | 14.15 | 1.23 | 37.89 | 7.74 |
| 1 paw in box | 1.42 | 0.38 | 7.07 | 2.44 |
| 2 paws in box | 2.83 | 1.56 | 30.95 | 17.54 |
| 3 paws in box | 1.25 | 0.25 | 5.39 | 1.19 |
| 4 paws in box | 33.1 | 4.71 | 37.88 | 9.59 |

Table 14 below provides the frequency and duration of tail positions. No differences between environments were found.

TABLE 14

|  | Enriched Environment | | Standard Collection Environment | |
|---|---|---|---|---|
|  | M | SE | M | SE |
| Frequency of Tail Positions Pre-Urination | | | | |
| Inverted U-tail | 0.08 | 0.04 | 0.17 | 0.12 |
| Wagging | 0.57 | 0.14 | 0.44 | 0.18 |
| Swish | 0.08 | 0.04 | 0.22 | 0.10 |
| Candy Cane | 0 | 0 | 0 | 0 |
| Twitch | 0.40 | 0.16 | 0.78 | 0.26 |
| Duration of Tail Positions Pre-Urination (Sec) | | | | |
| Inverted U-tail | 0.43 | 0.28 | 0.89 | 0.50 |
| Wagging | 1.27 | 0.59 | 2.92 | 2.11 |
| Swish | 0.23 | 0.15 | 0.54 | 0.32 |
| Candy Cane | 0 | 0 | 0 | 0 |
| Twitch | 0.96 | 0.43 | 2.47 | 1.10 |

Regarding box zones, Table 15 below depicts the location within the litter box when housed in the Enriched Environment. The frequency chart shows the mean frequency cats entered each zone, whereas the duration chart shows the mean duration cats were in each zone. When in the Enriched Environment, cats entered multiple zones and spent several seconds in each zone before urinating.

TABLE 15

Enriched Environment Location Pre-Urination (Frequency)

| Zone 1 | Zone 2 | Zone 3 |
|---|---|---|
| M = 0.85 | M = 1.22 | M = 0.85 |
| (SE = 0.13) | (SE = 0.18) | (SE = 0.13) |
| Zone 4 | Zone 5 | Zone 6 |
| M = 0.98 | M = 1.23 | M=1.15 |
| (SE = 0.17) | (SE = 0.21) | (SE = 0.20) |
| Zone 7 | Zone 8 | Zone 9 |
| M = 1.23 | M = 1.50 | M = 1.18 |
| (SE = 0.17) | (SE = .20) | (SE = 0.22) |

Enriched Environment Location Pre-Urination (Duration)

| Zone 1 | Zone 2 | Zone 3 |
|---|---|---|
| M = 3.29 | M = 3.27 | M = 4.29 |
| (SE = 0.68) | (SE = 0.67) | (SE = 0.89) |
| Zone 4 | Zone 5 | Zone 6 |
| M = 2.98 | M = 3.21 | M = 3.29 |
| (SE = 0.69) | (SE = 0.78) | (SE = 0.77) |
| Zone 7 | Zone 8 | Zone 9 |
| M = 6.52 | M = 7.67 | M = 6.64 |
| (SE = 1.92) | (SE = 2.66) | (SE = 1.87) |

Table 16 below depicts location within the litter box when housed in the Standard Collection Environment. The frequency chart shows the mean frequency cats entered each zone, whereas the duration chart shows the mean duration cats spent in each zone. When in the Standard Collection Environment, cats entered multiple zones and spent several seconds in each zone before urinating.

TABLE 16

Standard Collection Environment Location Pre-Urination (Frequency)

| Zone 1 | Zone 2 |
|---|---|
| M = 5.89 | M = 5.22 |
| (SB = 0.93) | (SE = 1.13) |
| Zone 3 | Zone 4 |
| M = 5.89 | M = 6.33 |
| (SE = 0.93) | (SE = 1.20) |

Standard Collection Environment Pre-Urination (Duration)

| Zone 1 | Zone 2 |
|---|---|
| M = 31.22 | M = 13.92 |
| (SE = 16.06) | (SE = 4.31) |
| Zone 3 | Zone 4 |
| M= 15.54 | M= 18.30 |
| (SE = 2.60) | (SE = 4.31) |

Pre-Urination Segment Summary

Listed below are the behavioral differences found between the two environments.

When in the Standard Collection Environment, cats pivoted more frequently (4 vs.1).

When in the Standard Collection Environment, cats sniffed other objects more often (4 vs. 1).

When in the Standard Collection Environment, cats sniffed objects for a greater duration (15 vs. 2).

When in the Standard Collection Environment, cats engaged in more frequent pawing (0 vs. 1).

When in the Standard Collection Environment, cats pawed for a greater duration (3 sec vs. 0 sec).

When in the Standard Collection Environment, cats had one paw in the box more frequently (5 vs. 1).

During Urination Segment

This section describes the during urination segment and compares the frequency and duration of the behaviors between the two environments.

Regarding body postures, Table 17 below presents the frequency and duration cats spent in the urination posture. Cats did not stand, sit, lie down, stretch, stand upright, or show incomplete elimination postures during urinations. When in the Standard Collection Environment, cats spent more time in the urination posture, $X(1)=8.33$, $p=0.004$.

TABLE 17

Urination Posture During Urination

|  | Enriched Environment | | Standard Collection Environment | |
| --- | --- | --- | --- | --- |
|  | M | SE | M | SE |
| Frequency | 0.98 | 0.03 | 1.00 | 0 |
| Duration (Sec) | 18.33 | 1.16 | 43.89 | 7.53 |

Regarding body movements, cats did not walk or pivot.

Furthermore, cats did not interact with objects, show vigilance, eat/drink, groom or shake.

Regarding ear wings, Table 18 below depicts the frequency and duration of the ear wing position. No differences between environments were found.

TABLE 18

Ear Wing Position During Urination

|  | Enriched Environment | | Standard Collection Environment | |
| --- | --- | --- | --- | --- |
|  | M | SE | M | SE |
| Frequency | 0.53 | 0.09 | 0.39 | 0.20 |
| Duration (Sec) | 5.38 | 0.94 | 4.10 | 2.16 |

Table 19 below provides the frequency and duration of flexes. No differences between environments were found.

TABLE 19

Flex During Urination

|  | Enriched Environment | | Standard Collection Environment | |
| --- | --- | --- | --- | --- |
|  | M | SE | M | SE |
| Frequency | 0.03 | 0.03 | 0 | 0 |
| Duration (Sec) | 0.23 | 0.23 | 0 | 0 |

Table 20 below presents the frequency and duration of eye squints. No differences between environments were found.

TABLE 20

Eye Squint During Urination

|  | Enriched Environment | | Standard Collection Environment | |
| --- | --- | --- | --- | --- |
|  | M | SE | M | SE |
| Frequency | 0.35 | 0.08 | 0.39 | 0.16 |
| Duration (Sec) | 3.59 | 0.92 | 11.89 | 6.10 |

Table 21 below illustrates frequency and duration of over the shoulder looks. No differences between environments were found.

TABLE 21

Over the Shoulder Look During Urination

|  | Enriched Environment | | Standard Collection Environment | |
| --- | --- | --- | --- | --- |
|  | M | SE | M | SE |
| Frequency | 0.33 | 0.08 | 0.39 | 0.11 |
| Duration (Sec) | 1.67 | 0.45 | 9.74 | 4.94 |

Regarding sniff/taste behavior, cats did not sniff or taste.

Furthermore, cats did not engage in paw motions.

Regarding balancing, Table 22 below shows the frequency and duration that cats balanced on the litter box. No differences between environments were found.

TABLE 22

Balancing During Urination

|  | Enriched Environment | | Standard Collection Environment | |
| --- | --- | --- | --- | --- |
|  | M | SE | M | SE |
| Frequency | 0 | 0 | 0.17 | 0.09 |
| Duration (Sec) | 0 | 0 | 9.45 | 5.31 |

Regarding paw position, Table 23 below provides the frequency and duration of the five paw positions relative to the litter box. When urinating in the Standard Collection Environment, cats were in the three paws in box stance more frequently, $X(1)=7.00$, $p=0.008$.

TABLE 23

|  | Enriched Environment | | Standard Collection Environment | |
| --- | --- | --- | --- | --- |
|  | M | SE | M | SE |
| Frequency of Paw Positions During Urination | | | | |
| 0 paws in box | 0 | 0 | 0.06 | 0.06 |
| 1 paw in box | 0 | 0 | 0 | 0 |
| 2 paws in box | 0 | 0 | 0 | 0 |
| 3 paws in box | 0 | 0 | 0.61 | 0.14 |
| 4 paws in box | 1.00 | 0 | 1.00 | 0.08 |
| Duration of Paw Positions During Urination (Sec) | | | | |
| 0 paws in box | 0 | 0 | 6.05 | 6.05 |
| 1 paw in box | 0 | 0 | 0 | 0 |
| 2 paws in box | 0 | 0 | 0 | 0 |
| 3 paws in box | 0 | 0 | 9.42 | 5.30 |
| 4 paws in box | 18.32 | 1.16 | 28.31 | 7.05 |

Regarding tail positions, Table 24 below gives the frequency and duration of the tail positions. When urinating in the Standard Collection Environment, cats displayed the inverted U-tail position for a greater duration, $X(1)=8.33$, $p=0.004$.

TABLE 24

| | Enriched Environment | | Standard Collection Environment | |
|---|---|---|---|---|
| | M | SE | M | SE |
| Frequency of Tail Positions During Urination | | | | |
| Inverted U-tail | 1.00 | 0.05 | 0.83 | 0.90 |
| Wagging | 0.68 | 0.08 | 0.28 | 0.11 |
| Swish | 0 | 0 | 0 | 0 |
| Candy Cane | 0.05 | 0.03 | 0.06 | 0.06 |
| Twitch | 0.03 | 0.03 | 0.56 | 0.56 |
| Duration of Tail Positions During Urination (Sec) | | | | |
| Inverted U-tail | 13.79 | 1.07 | 39.18 | 80.1 |
| Wagging | 2.52 | 0.45 | 0.99 | 0.41 |
| Swish | 0 | 0 | 0 | 0 |
| Candy Cane | 0.74 | 0.62 | 0.83 | 0.83 |
| Twitch | 0.72 | 0.72 | 0.18 | 0.18 |

Regarding box zones, Table 25 below depicts the location in the litter box in the Enriched Environment. The frequency table shows the mean frequency cats entered each zone and the duration table shows the mean duration cats spent in each zone. The results below indicate that when in the Enriched Environment, cats use the entire box to some degree.

TABLE 25

| Enriched Environment During Urination Location (Frequency) | | |
|---|---|---|
| Zone 1 | Zone 2 | Zone 3 |
| M = 0.25 | M = 0.28 | M = 0.20 |
| (SE = 0.10) | (SE = 0.08) | (SE = 0.08) |
| Zone 4 | Zone 5 | Zone 6 |
| M = 0.23 | M = 0.08 | M = 0.18 |
| (SE = 0.08) | (SE = 0.04) | (SE = 0.06) |
| Zone 7 | Zone 8 | Zone 9 |
| M = 0.13 | M = 0.20 | M = 0.18 |
| (SE = 0.05) | (SE = 0.08) | (SE = 0.07) |
| Enriched Environment During Urination Location (Duration) | | |
| Zone 1 | Zone 2 | Zone 3 |
| M = 0.78 | M = 3.27 | M = 1.86 |
| (SE = 0.48) | (SE = 1.01) | (SE = 0.95) |
| Zone 4 | Zone 5 | Zone 6 |
| M = 3.84 | M = 0.42 | M = 2.12 |
| (SE = 1.37) | (SE = 0.42) | (SE = 0.84) |
| Zone 7 | Zone 8 | Zone 9 |
| M = 1.57 | M = 1.82 | M = 2.39 |
| (SE = 0.77) | (SE = 0.96) | (SE = 1.31) |

Table 26 below depicts cat location in the litter box in the Standard Collection Environment. The results below indicate that when in the Standard Collection Environment, cats use the entire box to some degree.

TABLE 26

| Standard Collection Environment During Urination Location (Frequency) | |
|---|---|
| Zone 1 | Zone 2 |
| M = 0.50 | M = 0.61 |
| (SE = 0.12) | (SE = 0.14) |
| Zone 3 | Zone 4 |
| M = 0.33 | M = 0.44 |
| (SE = 0.14) | (SE = 0.18) |
| Standard Collection Environment During Urination Location (Duration) | |
| Zone 1 | Zone 2 |
| M = 15.71 | M = 10.45 |
| (SE = 5.85) | (SE = 6.99) |
| Zone 3 | Zone 4 |
| M = 9.23 | M = 1.47 |
| (SE = 4.04) | (SE = 1.47) |

During Urination Summary

Listed below are the behavioral differences found between the two environments.

When in the Standard Collection Environment, cats spend more time in the urination posture (52 sec vs. 20 sec).

When in the Standard Collection Environment, cats show the three paws in box stance more often (1 vs. 0).

When urinating in the Standard Collection Environment, cats display the inverted U-tail position for a greater duration (39 sec vs. 14 sec).

Post-Urination Segment

This section describes the post-urination segment and compares the frequency and duration of the behaviors between the two environments.

Table 27 below shows the frequency and duration of body postures performed by cats. In the Standard Collection Environment, cats stood more often, $X(1)=6.40$, $p=0.01$, and for a longer duration, $X(1)=12.00$, $p=0.0005$. Likewise, they were upright more frequently in the Standard Collection Environment, $X(1)=7.00$, $p=0.008$, and for a greater duration, $X(1)=7.00$, $p=0.008$.

TABLE 27

| | Enriched Environment | | Standard Collection Environment | |
|---|---|---|---|---|
| | M | SE | M | SE |
| Frequency of Postures Post-Urination | | | | |
| Stand | 1.38 | 0.17 | 1.94 | 0.22 |
| Sit | 0.50 | 0.19 | 1.06 | 0.19 |
| Lay | 0.05 | 0.05 | 0 | 0 |
| Stretch | 0 | 0 | 0 | 0 |
| Upright | 0 | 0 | 0.61 | 0.16 |
| Incomplete elimination posture | 0 | 0 | 0 | 0 |
| Duration of Postures Post-Urination (Sec) | | | | |
| Stand | 51.07 | 4.27 | 197.31 | 35.33 |
| Sit | 14.48 | 10.3 | 16.79 | 8.67 |
| Lay | 0.66 | 0.66 | 0 | 0 |
| Stretch | 0 | 0 | 0 | 0 |
| Upright | 0 | 0 | 5.02 | 1.85 |
| Incomplete elimination posture | 0 | 0 | 0 | 0 |

Table 28 below presents the frequency and duration of body movements. Cats pivoted more often in the Standard Collection Environment, $X(1)=7.36$, $p=0.007$, and for a longer duration, $X(1)=8.33$, $p=0.004$.

TABLE 28

| | Enriched Environment | | Standard Collection Environment | |
|---|---|---|---|---|
| | M | SE | M | SE |
| Frequency of Body Movements Post-Urination | | | | |
| Locomotion | 1.80 | 0.20 | 4.12 | 1.34 |
| Pivot | 1.32 | 0.15 | 2.44 | 0.42 |
| Duration of Body Movements Post-Urination (Sec) | | | | |
| Locomotion | 8.53 | 0.57 | 17.47 | 4.87 |
| Pivot | 4.16 | 0.54 | 12.32 | 3.55 |

Table 29 below shows the frequency and duration of interactions with objects. No differences between environments were found.

TABLE 29

Interactions with Objects Post-Urination

|  | Enriched Environment | | Standard Collection Environment | |
|---|---|---|---|---|
|  | M | SE | M | SE |
| Frequency | 0.40 | 0.21 | 1.63 | 0.71 |
| Duration (Sec) | 2.65 | 1.57 | 9.73 | 6.38 |

Table 30 below gives the frequency and duration of vigilance. Cats showed vigilance more frequently when housed in the Standard Collection Environment, X(1)=7.36, p=0.007, than in the Enriched Environment.

TABLE 30

Vigilance Post-Urination

|  | Enriched Environment | | Standard Collection Environment | |
|---|---|---|---|---|
|  | M | SE | M | SE |
| Frequency | 1.20 | 0.18 | 2.83 | 0.69 |
| Duration (Sec) | 3.31 | 0.50 | 11.30 | 3.12 |

Table 31 below provides the frequency and duration of eating/drinking. No differences between environments were found.

TABLE 31

Eating/Drinking Post-Urination

|  | Enriched Environment | | Standard Collection Environment | |
|---|---|---|---|---|
|  | M | SE | M | SE |
| Frequency | 0.03 | 0.03 | 0.13 | 0.13 |
| Duration (Sec) | 0.13 | 0.13 | 1.68 | 0.98 |

Table 32 below provides the frequency and duration of grooming. No differences between environments were found.

TABLE 32

Grooming Post-Urination

|  | Enriched Environment | | Standard Collection Environment | |
|---|---|---|---|---|
|  | M | SE | M | E |
| Frequency | 0.08 | 0.04 | 0.94 | 0.61 |
| Duration (Sec) | 1.36 | 0.89 | 9.68 | 7.87 |

Regarding shake movements, Table 33 below shows the frequency of the three types of shaking behavior. When housed in the Standard Collection Environment, cats shook their bodies less frequently, X(1)=7.00, p=0.0008.

TABLE 33

Frequency of Shakes Post-Urination

|  | Enriched Environment | | Standard Collection Environment | |
|---|---|---|---|---|
|  | M | SE | M | SE |
| Head Shake | 0.93 | 0.25 | 0.28 | 0.18 |
| Body Shake | 0.33 | 0.08 | 0 | 0 |
| Paw Shake | 0.83 | 0.13 | 1.44 | 0.88 |

Regarding sniff/taste, Table 34 below provides frequency and duration for sniffing and tasting behavior. When housed in the Standard Collection Environment, cats sniffed the litter less frequently, X(1)=8.00, p=0.005, and for a shorter duration, X(1)=8.00, p=0.005. When housed in the Standard Collection Environment, cats sniffed eliminations more frequently, X(1)=12.00, p=0.0005, and for a greater duration, X(1)=12.00, p=0.0005. Cats also sniffed other objects more frequently, X(1)=10.00, p=0.002, and for a greater duration when housed in the Standard Collection Environment, X(1)=12.00, p=0.0005.

TABLE 34

|  | Enriched Environment | | Standard Collection Environment | |
|---|---|---|---|---|
|  | M | SE | M | SE |
| Frequency Sniffing/Tasting Post-Urination | | | | |
| Sniff Litter | 1.38 | 0.75 | 0.06 | 0.06 |
| Sniff Elimination | 3.30 | 0.51 | 9.33 | 1.49 |
| Sniff Other | 0.65 | 0.16 | 4.39 | 1.00 |
| Taste Litter | 0.30 | 0.28 | 0 | 0 |
| Duration of Sniffing/Tasting Post-Urination (Sec) | | | | |
| Sniff Litter | 4.85 | 3.41 | 0.33 | 0.33 |
| Sniff Elimination | 10.69 | 2.67 | 26.25 | 4.31 |
| Sniff Other | 1.88 | 0.44 | 10.74 | 3.6 |
| Taste Litter | 1.17 | 1.07 | 0 | 0 |

Table 35 below presents the frequency and duration of paw motions. Compared to cats in the Enriched Environment, cats in the Standard Collection Environment touched substrates with their paws more often, X(1)=12.00, p=0.0005, and for a greater duration, X(1)=12.00, p=0.0005.

TABLE 35

|  | Enriched Environment | | Standard Collection Environment | |
|---|---|---|---|---|
|  | M | SE | M | SE |
| Frequency of Paw Motions Post-Urination | | | | |
| Pawing | 0.13 | 0.08 | 12.39 | 2.65 |
| Digging | 0.10 | 0.06 | 0 | 0 |
| Covering | 3.00 | 0.34 | 4.39 | 2.41 |
| Duration of Paw Motions Post-Urination (Sec) | | | | |
| Pawing | 0.47 | 0.39 | 96.58 | 24.98 |
| Digging | 0.56 | 0.35 | 0 | 0 |
| Covering | 15.08 | 1.20 | 5.58 | 2.38 |

Regarding balancing, Table 35 below gives the frequency and duration that cats balanced on the litter box sides. No differences between environments were found.

TABLE 35

| Balancing Post-Urination | | | | |
|---|---|---|---|---|
| | Enriched Environment | | Standard Collection Environment | |
| | M | SE | M | SE |
| Frequency | 0.23 | 0.07 | 0.50 | 0.26 |
| Duration (Sec) | 1.81 | 0.67 | 4.29 | 2.75 |

Table 36 below gives the frequency and duration of the five paw positions relative to the litter box. In the Standard Collection Environment, cats had zero paws in the box more frequently, $X(1)=12.00$, $p=0.0005$, and for a greater duration, $X(1)=12.00$, $p=0.0005$. Likewise in the Standard Collection Environment, cats had one paw in the box more frequently, $X(1)=11.00$, $p=0.0009$, and for a greater duration, $X(1)=12.00$, $p=0.0005$. Cats also showed the two paws in the litter box stance more frequently in the Standard Collection Environment, $X(1)=11.00$, $p=0.0009$. When in the Enriched Environment, cats had four paws in the litter box for a greater duration, $X(1)=12.00$, $p=0.0005$.

TABLE 36

| | Enriched Environment | | Standard Collection Environment | |
|---|---|---|---|---|
| | M | SE | M | SE |
| Frequency of Paw Positions Post-Urination | | | | |
| 0 paws in box | 1.10 | 0.08 | 3.50 | 0.47 |
| 1 paw in box | 1.03 | 0.13 | 5.50 | 0.97 |
| 2 paws in box | 1.15 | 0.12 | 3.17 | 0.53 |
| 3 paws in box | 0.98 | 0.11 | 1.06 | 0.21 |
| 4 paws in box | 1.13 | 0.06 | 0.67 | 0.16 |
| Duration of Paw Positions Post-Urination (Sec) | | | | |
| 0 paws in box | 15.08 | 2.28 | 175.99 | 40.28 |
| 1 paw in box | 1.08 | 0.27 | 17.32 | 4.68 |
| 2 paws in box | 1.48 | 0.42 | 18.09 | 4.22 |
| 3 paws in box | 0.66 | 0.11 | 1.21 | 0.47 |
| 4 paws in box | 49.35 | 12.87 | 3.42 | 1.77 |

Table 37 below provides the frequency and duration of the five tail positions. When housed in the Standard Collection Environment, cats wagged their tail less often, $X(1)=6.00$, $p=0.01$, and for a shorter duration, $X(1)=6.00$, $p=0.01$.

TABLE 37

| | Enriched Environment | | Standard Collection Environment | |
|---|---|---|---|---|
| | M | SE | M | SE |
| Frequency of Tail Positions Post-Urination | | | | |
| Inverted U-tail | 0 | 0 | 0 | 0 |
| Wagging | 0.23 | 0.09 | 0 | 0 |
| Swish | 0.10 | 0.06 | 0.06 | 0.06 |
| Candy Cane | 0 | 0 | 0 | 0 |
| Twitch | 0.50 | 0.18 | 0.28 | 0.19 |
| Duration of Tail Positions Post-Urination (Sec) | | | | |
| Inverted U-tail | 0 | 0 | 0 | 0 |
| Wagging | 0.95 | 0.40 | 0 | 0 |
| Swish | 0.42 | 0.26 | 0.09 | 0.09 |
| Candy Cane | 0 | 0 | 0 | 0 |
| Twitch | 14.93 | 1.17 | 0.70 | 0.54 |

Regarding box zones, Table 38 below depicts the location within the litter box when housed in the Enriched Environment. The frequency table shows the mean frequency cats entered each box zone. The duration table shows the mean duration cats spent in each box zone. The results below indicate that when in the Enriched Environment, cats used the entire box to some degree.

TABLE 38

| Enriched Environment Location (Frequency) | | |
|---|---|---|
| Zone 1 | Zone 2 | Zone 3 |
| M = 0.63 | M = 0.78 | M = 0.55 |
| (SE = 0.16) | (SE = 0.18) | (SE = 0.16) |
| Zone 4 | Zone 5 | Zone 6 |
| M = 0.80 | M = 1.20 | M = 0.63 |
| (SE = 0.20) | (SE = 0.33) | (SE = 0.17) |
| Zone 7 | Zone 8 | Zone 9 |
| M = 0.73 | M = 0.98 | M = 0.68 |
| (SE = 0.24) | (SE = .27) | (SE = 0.12) |
| Enriched Environment Location (Duration) | | |
| Zone 1 | Zone 2 | Zone 3 |
| M = 6.53 | M = 6.43 | M = 3.36 |
| (SE = 2.36) | (SE = 2.51) | (SE = 1.01) |
| Zone 4 | Zone 5 | Zone 6 |
| M = 2.90 | M = 10.73 | M = 4.04 |
| (SE = 0.88) | (SE = 6.27) | (SE = 1.57) |
| Zone 7 | Zone 8 | Zone 9 |
| M = 4.65 | M = 8.24 | M = 5.59 |
| (SE = 1.83) | (SE = 2.68) | (SE = 1.73) |

Table 39 below depicts the location within the litter box when housed in the Standard Collection Environment. The frequency table shows the mean frequency the cats entered each box zone. The duration table shows the mean duration cats spent in each box zone. The data indicates that cats are frequently moving about the box.

TABLE 39

| Standard Collection Environment Location Post-Urination (Frequency) | |
|---|---|
| Zone 1 | Zone 2 |
| M = 4.72 | M = 6.39 |
| (SE = 0.82) | (SE = 0.87) |
| Zone 3 | Zone 4 |
| M = 3.33 | M = 5.94 |
| (SE = 0.86) | (SE = 0.63) |
| Standard Collection Environment Location Post-Urination (Duration) | |
| Zone 1 | Zone 2 |
| M = 21.48 | M = 16.66 |
| (SE = 3.95) | (SE = 2.81) |
| Zone 3 | Zone 4 |
| M = 15.38 | M = 18.34 |
| (SE = 5.22) | (SE = 2.87) |

Post Urination Summary

Listed below are the behavioral differences found between the two environments.

When in the Standard Collection Environment the post-urination segment was longer (253 sec vs. 66 sec).

When in the Standard Collection Environment cats stood more often (2 standard vs. 1) and for a longer duration (227 sec vs. 49 sec).

When in the Standard Collection Environment cats pivoted more often (4 vs. 1) and for a longer duration (15 sec vs. 4 sec).

When in the Standard Collection Environment cats were more vigilant (3 vs. 1).

When in the Standard Collection Environment cats pawed more frequently (12 vs. 0) and for a greater duration (97 sec vs. 1).

When in the Standard Collection Environment cats sniffed eliminations more frequently (10 vs. 3) and for a greater duration (29 sec vs. 11 sec).

When in the Standard Collection Environment cats sniffed other objects more frequently, (5 sec vs. 1 sec), and for a greater duration (13 sec vs. 2 sec).

When in the Standard Collection Environment cats had zero paws in the box more frequently (3 vs. 1), and for a greater duration (213 sec vs. 14 sec).

When in the Standard Collection Environment cats had one paw in the box more frequently (5 vs. 1) and for a greater duration (17 sec vs. 1 sec).

When in the Standard Collection Environment cats shook their bodies less frequently (0 vs. 1).

When in the Standard Collection Environment cats sniffed the litter less frequently (0 vs.1) and for a shorter duration (0 sec vs. 5 sec).

When in the Standard Collection Environment cats wagged their tails for a shorter duration (0 sec vs. 1 sec).

Defecation Events

Figure 6:
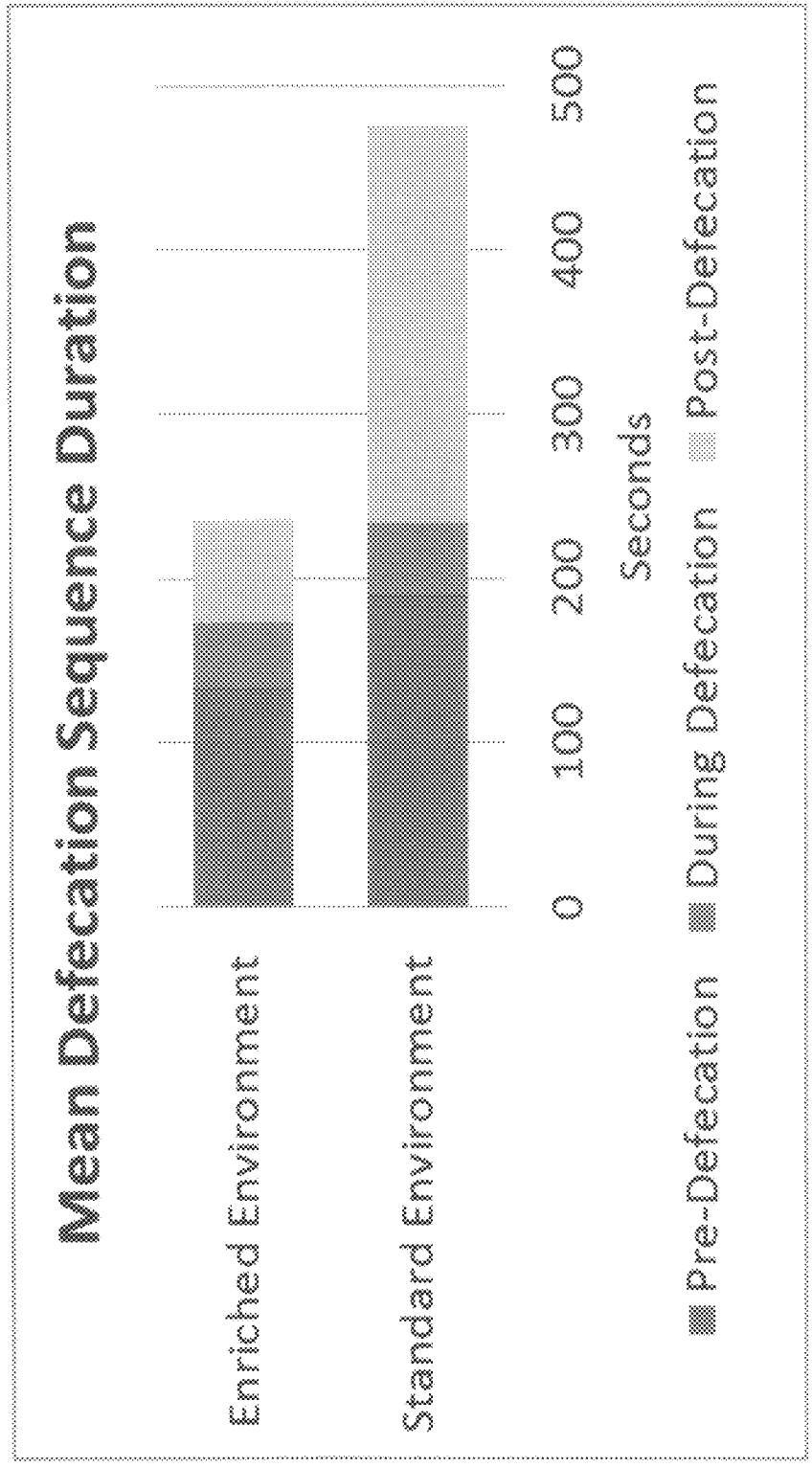

Table 2 above provides the number of cat defecation events that were coded, and FIG. 6 depicts the duration spent in the three elimination sequence segments (pre-, during, and post-elimination) for both environment types during the observed defecation events. In the Standard Collection Environment, the duration of the overall defecation sequence, from pre- to post-defecation, was longer, $X(1)=8.00$, $p=0.005$, than in the Enriched Environment. The duration of the post-defecation segment was significantly longer when cats were housed in the Standard Collection Environment, $X(1)=8.00$, $p=0.005$, than in the Enriched Environment.

Pre-Defecation Segment

Regarding body postures, cat standing, sitting, lying down, stretch, stand upright, and incomplete elimination postures were observed. Table 40 below displays the frequency and duration of these postures.

TABLE 40

|  | Enriched Environment | | Standard Collection Environment | |
| --- | --- | --- | --- | --- |
|  | M | SE | M | SE |
| Frequency of Postures Pre-Defecation | | | | |
| Stand | 3.36 | 0.85 | 2.90 | 0.78 |
| Sit | 0.64 | 0.29 | 1.60 | 0.56 |
| Lay | 0.36 | 0.20 | 0.80 | 0.39 |
| Stretch | 0.14 | 0.10 | 0.40 | 0.22 |
| Upright | 0 | 0 | 0.10 | 0.10 |
| Incomplete elimination posture | 1.71 | 0.67 | 0.30 | 0.15 |
| Duration of Postures Pre-Defecation (Sec) | | | | |
| Stand | 115.30 | 27.37 | 158.33 | 43.03 |
| Sit | 6.79 | 4.58 | 23.51 | 11.95 |
| Lay | 6.22 | 4.22 | 10.12 | 6.88 |
| Stretch | 0.56 | 0.41 | 1.14 | 0.64 |
| Upright | 0 | 0 | 0.12 | 0.12 |
| Incomplete elimination posture | 13.31 | 6.98 | 0.83 | 0.43 |

Table 41 below provides the frequency and durations of body movements. Cats pivoted more frequently in the Standard Collection Environment, $X(1)=6.00$, $p=0.01$.

TABLE 41

|  | Enriched Environment | | Standard Collection Environment | |
| --- | --- | --- | --- | --- |
|  | M | SE | M | SE |
| Frequency of Body Movements Pre-Defecation | | | | |
| Locomotion | 3.79 | 0.81 | 3.30 | 1.14 |
| Pivot | 2.00 | 0.60 | 3.20 | 0.77 |
| Duration of Body Movements Pre-Defecation (Sec) | | | | |
| Locomotion | 18.46 | 3.86 | 22.12 | 9.12 |
| Pivot | 7.07 | 2.02 | 10.85 | 3.04 |

Table 42 below shows the frequency and duration of interactions with objects. No differences between environments were found.

TABLE 42

|  | Enriched Environment | | Standard Collection Environment | |
| --- | --- | --- | --- | --- |
|  | M | SE | M | SE |
| Interactions with Objects Pre-Defecation | | | | |
| Frequency | 0.14 | 0.10 | 1.20 | 0.71 |
| Duration (Sec) | 0.31 | 0.24 | 11.70 | 9.72 |

Table 43 below gives the frequency and duration of vigilance. No differences between environments were found.

TABLE 43

|  | Enriched Environment | | Standard Collection Environment | |
| --- | --- | --- | --- | --- |
|  | M | SE | M | SE |
| Vigilance Pre-Defecation | | | | |
| Frequency | 3.64 | 1.11 | 2.60 | 1.63 |
| Duration (Sec) | 19.78 | 7.18 | 7.81 | 5.15 |

Table 44 below presents the frequency and duration of eating/drinking. No differences between environments were found.

TABLE 44

|  | Enriched Environment | | Standard Collection Environment | |
| --- | --- | --- | --- | --- |
|  | M | SE | M | SE |
| Eating/Drinking Pre-Defecation | | | | |
| Frequency | 0 | 0 | 0.50 | 0.27 |
| Duration (sec) | 0 | 0 | 0.82 | 0.55 |

Table 45 below presents the frequency and duration of grooming. No differences between environments were found.

TABLE 45

Grooming Pre-Defecation

| | Enriched Environment | | Standard Collection Environment | |
|---|---|---|---|---|
| | M | SE | M | SE |
| Frequency | 0.50 | 0.25 | 0.60 | 0.22 |
| Duration (Sec) | 1.46 | 0.72 | 4.56 | 2.20 |

Regarding shake movements, Table 46 below presents the frequency of the three types of shaking behavior. No differences between environments were found.

TABLE 46

Frequency of Shakes Pre-Defecation

| | Enriched Environment | | Standard Collection Environment | |
|---|---|---|---|---|
| | M | SE | M | SE |
| Head Shake | 1.86 | 0.77 | 0.50 | 0.17 |
| Body Shake | 0.36 | 0.23 | 0.10 | 0.10 |
| Paw Shake | 1.43 | 0.68 | 1.00 | 0.39 |

Table 47 below provides the frequency and duration of sniffing and tasting behaviors. When housed in the Standard Collection Environment, cats sniffed the litter for a shorter duration, $X(1)=8.00$, $p=0.005$, and sniffed other objects in their environment for a longer duration, $X(1)=7.00$, $p=0.008$.

TABLE 47

| | Enriched Environment | | Standard Collection Environment | |
|---|---|---|---|---|
| | M | SE | M | SE |
| Frequency of Sniffing/Tasting Pre-Defecation | | | | |
| Sniff Litter | 8.07 | 1.33 | 2.50 | 0.17 |
| Sniff Elimination | 1.79 | 1.10 | 7.00 | 2.03 |
| Sniff Other | 1.07 | 0.41 | 6.40 | 1.81 |
| Taste Litter | 0.79 | 0.64 | 0 | 0 |
| Duration of Sniffing/Tasting Pre-Defecation (Sec) | | | | |
| Sniff Litter | 33.06 | 5.71 | 4.70 | 2.64 |
| Sniff Elimination | 10.24 | 7.92 | 26.69 | 8.03 |
| Sniff Other | 2.46 | 0.88 | 21.13 | 6.87 |
| Taste Litter | 8.63 | 8.35 | 0 | 0 |

Table 48 below displays the frequency and duration of paw motions. In the Standard Collection Environment cats pawed more frequently, $X(1)=6.00$, $p=0.01$, and for a greater duration, $X(1)=6.00$, $p=0.01$.

TABLE 48

| | Enriched Environment | | Standard Collection Environment | |
|---|---|---|---|---|
| | M | SE | M | SE |
| Frequency of Paw Motions Pre-Defecation | | | | |
| Pawing | 0 | 0 | 4.30 | 2.66 |
| Digging | 6.43 | 2.35 | 6.40 | 3.54 |
| Covering | 0.21 | 0.15 | 2.00 | 1.04 |

TABLE 48-continued

| | Enriched Environment | | Standard Collection Environment | |
|---|---|---|---|---|
| | M | SE | M | SE |
| Duration of Paw Motions Pre-Defecation (Sec) | | | | |
| Pawing | 0 | 0 | 21.76 | 13.31 |
| Digging | 50.38 | 11.10 | 38.87 | 21.03 |
| Covering | 1.00 | 0.78 | 7.37 | 7.37 |

Regarding balancing, Table 49 below presents the frequency and duration that cats balanced on the litter box sides. No differences between environments were found.

TABLE 49

Balancing Pre-Defecation

| | Enriched Environment | | Standard Collection Environment | |
|---|---|---|---|---|
| | M | SE | M | SE |
| Frequency | 0.21 | 0.11 | 0.40 | 0.22 |
| Duration (Sec) | 2.45 | 1.37 | 1.87 | 1.23 |

Table 50 below gives the frequency and duration of the five paw positions relative to the litter box (number of paws in the litter box). No differences between environments were found.

TABLE 50

| | Enriched Environment | | Standard Collection Environment | |
|---|---|---|---|---|
| | M | SE | M | SE |
| Frequency of Paw Positions Pre-Defecation | | | | |
| 0 paws in box | 1.14 | 0.10 | 4.00 | 1.32 |
| 1 paw in box | 1.29 | 0.19 | 6.10 | 2.28 |
| 2 paws in box | 1.19 | 0.19 | 4.10 | 1.51 |
| 3 paws in box | 1.29 | 0.19 | 2.20 | 0.65 |
| 4 paws in box | 1.14 | 0.10 | 1.40 | 0.37 |
| Duration of Paw Positions Pre-Defecation (Sec) | | | | |
| 0 paws in box | 16.71 | 2.67 | 86.84 | 27.35 |
| 1 paw in box | 0.85 | 0.16 | 8.43 | 3.22 |
| 2 paws in box | 2.54 | 0.89 | 55.00 | 30.53 |
| 3 paws in box | 0.95 | 0.17 | 3.27 | 1.59 |
| 4 paws in box | 121.43 | 40.12 | 39.67 | 21.75 |

Table 51 below provides the frequency and duration of the five tail positions. No differences between environments were found.

TABLE 51

| | Enriched Environment | | Standard Collection Environment | |
|---|---|---|---|---|
| | M | SE | M | SE |
| Frequency of Tail Positions Pre-Defecation | | | | |
| Inverted U-tail | 0 | 0 | 0.40 | 0.16 |
| Wagging | 0.43 | 0.17 | 0 | 0 |
| Swish | 0.79 | 0.37 | 0.30 | 0.21 |
| Candy Cane | 0.14 | 0.10 | 0 | 0 |
| Twitch | 1.43 | 0.54 | 0.90 | 0.80 |

TABLE 51-continued

|  | Enriched Environment | | Standard Collection Environment | |
|---|---|---|---|---|
|  | M | SE | M | SE |
| Duration of Tail Positions Pre-Defecation (Sec) | | | | |
| Inverted U-tail | 0 | 0 | 0.57 | 0.42 |
| Wagging | 1.80 | 0.76 | 0 | 0 |
| Swish | 2.89 | 1.41 | 1.28 | 1.07 |
| Candy Cane | 0.79 | 0.55 | 0 | 0 |
| Twitch | 2.97 | 1.90 | 2.85 | 2.51 |

Regarding box zones, Table 52 below depicts the location within the litter box when housed in the Enriched Environment. The frequency table shows the mean frequency cats entered each zone. The duration table shows the mean duration cats spent in each zone. The results from the Enriched Environment indicate that cats entered multiple box zones in the large litter box and spent on average between 6.53 and 23.32 seconds in each zone.

TABLE 52

Enriched Environment Pre-Defecation Location (Frequency)

| Zone 1 | Zone 2 | Zone 3 |
|---|---|---|
| M = 1.07 | M = 3.07 | M = 1.71 |
| (SE = 0.29) | (SE = 0.72) | (SE = 0.81) |
| Zone 4 | Zone 5 | Zone 6 |
| M = 2.21 | M = 3.29 | M = 2.57 |
| (SE = 0.28) | (SE = 0.55) | (SE = 0.68) |
| Zone 7 | Zone 8 | Zone 9 |
| M = 1.36 | M = 1.86 | M = 1.79 |
| (SE = 0.31) | (SE = 0.44) | (SE = 0.50) |

Enriched Environment Pre-Defecation Location (Duration)

| Zone 1 | Zone 2 | Zone 3 |
|---|---|---|
| M = 6.53 | M = 23.32 | M = 13.00 |
| (SE = 2.36) | (SE = 8.64) | (SE = 7.53) |
| Zone 4 | Zone 5 | Zone 6 |
| M = 11.18 | M = 17.73 | M = 14.21 |
| (SE = 1.87) | (SE = 5.09) | (SE = 5.25) |
| Zone 7 | Zone 8 | Zone 9 |
| M = 15.84 | M = 15.61 | M = 11.89 |
| (SE = 7.14) | (SE = 7.37) | (SE = 5.00) |

Table 53 below depicts the cat location within the litter box when housed in the Standard Collection Environment. The frequency table shows the mean frequency cats entered each zone. The duration table shows the mean duration cats spent in each zone. The results reveal cats frequently moved into all litter box zones in the Standard Collection Environment and spent on average between 14.90 and 60.92 seconds in each zone.

TABLE 53

Standard Collection Environment Pre-Defecation Location (Frequency)

| Zone 1 | Zone 2 |
|---|---|
| M = 6.90 | M = 7.10 |
| (SE = 1.27) | (SE = 1.86) |
| Zone 3 | Zone 4 |
| M = 5.00 | M = 6.00 |
| (SE = 0.95) | (SE = 1.21) |

TABLE 53-continued

Standard Collection Environment Pre-Defecation Location (Duration)

| Zone 1 | Zone 2 |
|---|---|
| M = 60.92 | M = 23.90 |
| (SE = 31.28) | (SE = 9.10) |
| Zone 3 | Zone 4 |
| M = 19.73 | M = 14.90 |
| (SE = 6.51) | (SE = 3.83) |

Pre-Defecation Summary

Listed below are the behavioral differences found between the two environments.

When in the Standard Collection Environment cats showed the incomplete elimination posture more often (2 vs. 0).

When in the Standard Collection Environment cats sniffed other objects in their environment for a longer duration (15 sec vs. 2 sec).

When in the Standard Collection Environment cats sniffed the litter for a shorter duration (5 sec vs. 32 sec).

When in the Standard Collection Environment cats pawed more frequently (4 vs. 0) and for a greater duration (22 sec vs. 0 sec).

During Defecation Segment

This section describes the during defecation segment and compares the frequency and duration of the behaviors between the two environments.

Regarding body postures, Table 54 below presents the frequency and duration in the defecation posture. Cats did not stand, sit, lie down, stretch, stand upright, or show incomplete elimination postures during defecation. No differences between environments were found.

TABLE 54

Defecation Postures During Defecation

|  | Enriched Environment | | Standard Collection Environment | |
|---|---|---|---|---|
|  | M | SE | M | SE |
| Frequency | 1.00 | 0 | 1.00 | 0 |
| Duration (Sec) | 45.19 | 4.41 | 38.27 | 4.75 |

Regarding body movements, cats did not walk or pivot.

Furthermore, cats did not interact with objects, show vigilance, eat/drink, groom or shake.

Table 55 below shows the frequency and duration of the ear wing position. No differences between environments were found.

TABLE 55

Ear Wing Position During Defecation

|  | Enriched Environment | | Standard Collection Environment | |
|---|---|---|---|---|
|  | M | SE | M | SE |
| Frequency | 0.79 | 0.15 | 0.40 | 0.16 |
| Duration (Sec) | 17.41 | 5.24 | 11.51 | 4.91 |

Table 56 below gives the frequency and duration of flexes. No differences between environments were found.

TABLE 56

Flex During Defecation

|  | Enriched Environment | | Standard Collection Environment | |
| --- | --- | --- | --- | --- |
|  | M | SE | M | SE |
| Frequency | 1.07 | 0.07 | 1.10 | 0.10 |
| Duration (Sec) | 13.76 | 3.21 | 21.71 | 6.58 |

Table 57 below shows the frequency and duration of eye squints. No differences between environments were found.

TABLE 57

Eye Squint During Defecation

|  | Enriched Environment | | Standard Collection Environment | |
| --- | --- | --- | --- | --- |
|  | M | SE | M | SE |
| Frequency | 0.57 | 0.14 | 0.20 | 0.13 |
| Duration (Sec) | 14.70 | 6.12 | 4.79 | 3.23 |

Table 58 below provides both frequency and duration of over the shoulder looks. No differences between environments were found.

TABLE 58

Over the Shoulder Look During Defecation

|  | Enriched Environment | | Standard Collection Environment | |
| --- | --- | --- | --- | --- |
|  | M | SE | M | SE |
| Frequency | 0.36 | 0.13 | 1.00 | 0.47 |
| Duration (Sec) | 1.46 | 0.66 | 5.87 | 3.06 |

Cats did not sniff or taste or engage in paw motions.

Regarding balancing, Table 59 below displays the frequency and duration that cats balanced on the litter box. No differences between environments were found.

TABLE 59

Balancing During Defecation

|  | Enriched Environment | | Standard Collection Environment | |
| --- | --- | --- | --- | --- |
|  | M | SE | M | SE |
| Frequency | 0 | 0 | 0.40 | 0.16 |
| Duration (Sec) | 0 | 0 | 22.34 | 11.16 |

Regarding paw positions, Table 60 below presents the frequency and duration of the five paw positions relative to the litter box. No differences between environments were found.

TABLE 60

|  | Enriched Environment | | Standard Collection Environment | |
| --- | --- | --- | --- | --- |
|  | M | SE | M | SE |
| Frequency of Paw Positions During Defecation | | | | |
| 0 paws in box | 0 | 0 | 0 | 0 |
| 1 paw in box | 0 | 0 | 0.20 | 0.13 |
| 2 paws in box | 0 | 0 | 0.30 | 0.15 |
| 3 paws in box | 0 | 0 | 0.50 | 0.17 |
| 4 paws in box | 1.00 | 0 | 0.80 | 0.13 |
| Duration of Paw Positions During Defecation (Sec) | | | | |
| 0 paws in box | 0 | 0 | 0 | 0 |
| 1 paw in box | 0 | 0 | 10.57 | 10.57 |
| 2 paws in box | 0 | 0 | 8.04 | 5.44 |
| 3 paws in box | 0 | 0 | 3.73 | 3.73 |
| 4 paws in box | 38.27 | 4.76 | 22.58 | 6.44 |

Regarding tail positions, Table 61 below gives the frequency and duration of five tail positions. No differences between environments were found.

TABLE 61

|  | Enriched Environment | | Standard Collection Environment | |
| --- | --- | --- | --- | --- |
|  | M | SE | M | SE |
| Frequency of Tail Positions During Defecation | | | | |
| Inverted U-tail | 0.43 | 0.14 | 1.00 | 0 |
| Wagging | 0.29 | 0.13 | 0 | 0 |
| Swish | 0.07 | 0.07 | 0 | 0 |
| Candy Cane | 0.29 | 0.13 | 0 | 0 |
| Twitch | 0.07 | 0.07 | 0 | 0 |
| Duration of Tail Positions During Defecation (Sec) | | | | |
| Inverted U-tail | 10.21 | 3.84 | 41.55 | 7.54 |
| Wagging | 1.19 | 0.65 | 0 | 0 |
| Swish | 0.98 | 0.98 | 0 | 0 |
| Candy Cane | 10.65 | 6.50 | 0 | 0 |
| Twitch | 0.01 | 0.01 | 0 | 0 |

Regarding box zones, Table 62 below depicts the location within the litter box when housed in the Enriched Environment. The frequency table shows the mean frequency cats entered each zone. The duration table shows the mean duration cats spent in each zone. The results below show that cats were in many different zones during defecations in the Enriched Environment, except for zones 2 and 3. On average cats spent between 2.03 and 10.12 seconds in each of zones 4 through 9.

TABLE 62

Enriched Environment During Defecation Location (Frequency)

| Zone 1 | Zone 2 | Zone 3 |
| --- | --- | --- |
| M = 0.14 | M = 0.07 | M = 0 |
| (SE = 0.10) | (SE = 0.07) | (SE = 0) |
| Zone 4 | Zone 5 | Zone 6 |
| M = 0.29 | M = 0.36 | M = 0.29 |
| (SE = 0.13) | (SE = 0.17) | (SE = 0.13) |
| Zone 7 | Zone 8 | Zone 9 |
| M = 0.29 | M = 0.14 | M = 0.07 |
| (SE = 0.13) | (SE = 0.10) | (SE = 0.07) |

Enriched Environment During Defecation Location (Duration)

| Zone 1 | Zone 2 | Zone 3 |
| --- | --- | --- |
| M = 4.54 | M = 0 | M = 0 |
| (SE = 3.45) | (SE = 0) | (SE = 0) |

TABLE 62-continued

| Zone 4 | Zone 5 | Zone 6 |
|---|---|---|
| M = 9.29 | M = 3.24 | M = 5.71 |
| (SE = 6.76) | (SE = 2.25) | (SE = 4.12) |
| Zone 7 | Zone 8 | Zone 9 |
| M = 10.12 | M = 2.71 | M = 2.03 |
| (SE = 4.53) | (SE = 2.71) | (SE = 2.03) |

Table 63 below depicts the location within the litter box when housed in the Standard Collection Environment. The frequency table shows the mean frequency cats entered each zone. The duration table shows the mean duration cats spent in each zone. The results below indicate that cats were utilizing all box zones in the Standard Collection Environment. The average time spent in each zone ranged from 4.46 to 18.78 seconds.

TABLE 63

Standard Collection Environment
During Defecation Location (Frequency)

| Zone 1 | Zone 2 |
|---|---|
| M = 0.40 | M = 0.60 |
| (SE = 0.16) | (SE = 0.22) |
| Zone 3 | Zone 4 |
| M = 0.40 | M = 0.20 |
| (SE = 0.16) | (SE = 0.13) |

Standard Collection Environment
During Defecation Location (Duration)

| Zone 1 | Zone 2 |
|---|---|
| M = 10.03 | M = 5.02 |
| (SE = 5.18) | (SE = 3.90) |
| Zone 3 | Zone 4 |
| M = 18.76 | M = 4.46 |
| (SE = 11.25) | (SE = 4.46) |

During Defecation Summary

No differences between environments were found during defecation.

Post-Defecation Segment

This section describes the post-defecation segment and compares the frequency and duration of the behaviors between the two environments.

Cat standing, sitting, lying down, stretch, standing upright, and incomplete elimination postures were recorded. Table 64 below provides the frequency and duration of these postures. In the Standard Collection Environment, cats stood (X(1)=8.00, p=0.005) and sat (X(1)=6.00, p=0.01) for longer duration.

TABLE 64

| | Enriched Environment | | Standard Collection Environment | |
|---|---|---|---|---|
| | M | SE | M | SE |
| Frequency of Postures Post-Defecation | | | | |
| Stand | 1.64 | 0.23 | 1.80 | 0.44 |
| Sit | 0 | 0 | 1.00 | 0.26 |
| Lay | 0.07 | 0.07 | 0.30 | 0.15 |
| Stretch | 0 | 0 | 0 | 0 |
| Upright | 0 | 0 | 0.60 | 0.43 |
| Incomplete elimination posture | 0.07 | 0.07 | 0 | 0 |
| Duration of Postures Post-Defecation (Sec) | | | | |
| Stand | 58.15 | 7.08 | 218.96 | 56.99 |
| Sit | 0 | 0 | 9.32 | 3.96 |
| Lay | 0.06 | 0.06 | 1.72 | 1.04 |
| Stretch | 0 | 0 | 0 | 0 |

TABLE 64-continued

| | Enriched Environment | | Standard Collection Environment | |
|---|---|---|---|---|
| | M | SE | M | SE |
| Upright | 0 | 0 | 4.11 | 3.69 |
| Incomplete elimination posture | 0.58 | 0.58 | 0 | 0 |

Table 65 below displays the frequency and durations of body movements. No differences between environments were found.

TABLE 65

| | Enriched Environment | | Standard Collection Environment | |
|---|---|---|---|---|
| | M | SE | M | SE |
| Frequency of Body Movements Post-Defecation | | | | |
| Locomotion | 2.21 | 0.35 | 2.75 | 0.70 |
| Pivot | 1.71 | 0.37 | 8.13 | 2.94 |
| Duration of Body Movements Post-Defecation (Sec) | | | | |
| Locomotion | 10.06 | 0.98 | 6.71 | 1.36 |
| Pivot | 6.48 | 2.05 | 24.52 | 10.50 |

Table 66 below presents the frequency and duration of interactions with objects. No differences between environments were found.

TABLE 66

Interactions with Objects Post-Defecation

| | Enriched Environment | | Standard Collection Environment | |
|---|---|---|---|---|
| | M | SE | M | SE |
| Frequency | 0.71 | 0.71 | 0.63 | 0.32 |
| Duration (Sec) | 0.16 | 0.16 | 0.26 | 0.26 |

Table 67 below gives the frequency and duration of vigilance. No differences between environments were found.

TABLE 67

Vigilance Post-Defecation

| | Enriched Environment | | Standard Collection Environment | |
|---|---|---|---|---|
| | M | SE | M | SE |
| Frequency | 1.43 | 0.36 | 1.50 | 0.54 |
| Duration (Sec) | 5.99 | 1.59 | 5.44 | 2.49 |

Table 68 below shows the frequency and duration of eating/drinking. No differences between environments were found.

TABLE 68

Eating/Drinking Post-Defecation

|  | Enriched Environment | | Standard Collection Environment | |
|---|---|---|---|---|
|  | M | SE | M | SE |
| Frequency | 0.07 | 0.07 | 0.25 | 0.16 |
| Duration (Sec) | 0.23 | 0.23 | 0.24 | 0.24 |

Table 69 below provides the frequency and duration of grooming. No differences between environments were found.

TABLE 69

Grooming Post-Defecation

|  | Enriched Environment | | Standard Collection Environment | |
|---|---|---|---|---|
|  | M | SE | M | SE |
| Frequency) | 0 | 0 | 0.60 | 0.31 |
| Duration (Sec) | 0 | 0 | 0.24 | 0.24 |

Regarding shake movements, Table 70 below displays the frequency of the three types of shaking behavior. No differences between environments were found.

TABLE 70

Frequency of Shakes Post-Defecation

|  | Enriched Environment | | Standard Collection Environment | |
|---|---|---|---|---|
|  | M | SE | M | SE |
| Head | 0.86 | 0.29 | 0.30 | 0.21 |
| Body | 0.64 | 0.22 | 0.20 | 0.13 |
| Paw | 1.36 | 0.32 | 0.70 | 0.30 |

Table 71 below presents the frequency and duration of sniffing and tasting behaviors. In the Standard Collection Environment, cats sniffed eliminations for a greater duration, $X(1)=8.00$, $p=0.005$.

TABLE 71

|  | Enriched Environment | | Standard Collection Environment | |
|---|---|---|---|---|
|  | M | SE | M | SE |
| Frequency of Sniffing/Tasting Post-Defecation | | | | |
| Sniff Litter | 8.07 | 1.33 | 0.60 | 0.60 |
| Sniff Elimination | 1.79 | 1.10 | 15.70 | 5.56 |
| Sniff Other | 1.07 | 0.41 | 2.40 | 0.54 |
| Taste Litter | 0.79 | 0.63 | 0 | 0 |
| Duration of Sniffing/Tasting Post-Defecation (Sec) | | | | |
| Sniff Litter | 6.58 | 3.37 | 3.54 | 3.54 |
| Sniff Elimination | 11.37 | 2.11 | 47.72 | 22.44 |
| Sniff Other | 0.47 | 0.27 | 6.04 | 1.70 |
| Taste Litter | 1.35 | 1.05 | 0 | 0 |

Table 72 below gives the frequency and duration of paw motions. When in the Standard Collection Environment, cats pawed more frequently, $X(1)=7.00$, $p=0.008$, and for a greater duration, $X(1)=7.00$, $p=0.008$.

TABLE 72

|  | Enriched Environment | | Standard Collection Environment | |
|---|---|---|---|---|
|  | M | SE | M | SE |
| Frequency of Paw Motions Post-Defecation | | | | |
| Pawing | 0.14 | 0.14 | 9.80 | 2.65 |
| Digging | 0.14 | 0.14 | 0 | 0 |
| Covering | 2.43 | 0.37 | 2.50 | 1.18 |
| Duration of Paw Motions Post-Defecation (Sec) | | | | |
| Pawing | 0.76 | 0.76 | 77.70 | 22.91 |
| Digging | 0.96 | 0.75 | 0 | 0 |
| Covering | 20.98 | 3.51 | 76.86 | 43.31 |

Regarding balancing, Table 73 below shows the frequency and duration that cats balanced on the litter box. No differences between environments were found.

TABLE 73

Balancing Post-Defecation

|  | Enriched Environment | | Standard Collection Environment | |
|---|---|---|---|---|
|  | M | E | M | SE |
| Frequency | 0.14 | 0.14 | 0.50 | 0.22 |
| Duration (Sec) | 1.91 | 1.91 | 2.86 | 1.28 |

Table 74 below provides the frequency and duration of five paw positions relative to litter box events. In the Standard Collection Environment, cats had zero paws in the box more frequently, $X(1)=6.00$, $p=0.01$, and for a greater duration, $X(1)=8.00$, $p=0.0005$. Likewise in the Standard Collection Environment, cats had one paw in the box more frequently, $X(1)=6.00$, $p=0.01$, and for a greater duration, $X(1)=8.00$, $p=0.0005$.

TABLE 74

|  | Enriched Environment | | Standard Collection Environment | |
|---|---|---|---|---|
|  | M | SE | M | SE |
| Frequency of Paw Positions Post-Defecation | | | | |
| 0 paws in box | 1.21 | 0.15 | 3.10 | 0.57 |
| 1 paw in box | 1.07 | 0.16 | 5.60 | 1.31 |
| 2 paws in box | 1.36 | 0.25 | 4.60 | 1.07 |
| 3 paws in box | 1.07 | 0.16 | 2.50 | 0.86 |
| 4 paws in box | 1.21 | 0.15 | 1.40 | 0.48 |
| Duration of Paw Positions Post-Defecation (Sec) | | | | |
| 0 paws in box | 11.63 | 0.96 | 70.05 | 20.61 |
| 1 paw in box | 0.63 | 0.16 | 26.40 | 12.37 |
| 2 paws in box | 2.29 | 1.19 | 42.40 | 14.84 |
| 3 paws in box | 0.68 | 0.17 | 6.83 | 3.69 |
| 4 paws in box | 45.41 | 6.61 | 88.43 | 59.94 |

Table 75 below displays the frequency and duration of the five tail positions. No differences between environments were found.

TABLE 75

|  | Enriched Environment | | Standard Collection Environment | |
|---|---|---|---|---|
|  | M | SE | M | SE |
| Frequency of Tail Positions Post-Defecation | | | | |
| Inverted U-tail | 0 | 0 | 0 | 0 |
| Wagging | 0.07 | 0.07 | 0 | 0 |
| Swish | 0.36 | 0.23 | 0.10 | 0.10 |
| Candy Cane | 0 | 0 | 0 | 0 |
| Twitch | 0.36 | 0.13 | 0 | 0 |
| Duration of Tail Positions Post-Defecation (Sec) | | | | |
| Inverted U-tail | 0 | 0 | 0 | 0 |
| Wagging | 0.18 | 0.18 | 0 | 0 |
| Swish | 0.90 | 0.54 | 0.07 | 0.07 |
| Candy Cane | 0 | 0 | 0 | 0 |
| Twitch | 0.73 | 0.31 | 0 | 0 |

Regarding box zones, Table 76 below depicts the location within the litter box when housed in the Enriched Environment. The frequency chart shows the mean frequency cats entered each zone. The duration table shows the mean duration cats spent in each zone. The results below indicate that cats were moving throughout the entire litter box, spending on average 1.50 to 12.10 seconds in each zone.

TABLE 76

Enriched Environment Post-Defecation Location (Frequency)

| Zone 1 | Zone 2 | Zone 3 |
|---|---|---|
| M = 0.57 | M = 1.07 | M = 0.14 |
| (SE = 0.25) | (SE = 0.43) | (SE = 0.14) |
| Zone 4 | Zone 5 | Zone 6 |
| M = 1.57 | M = 2.21 (SE = 0.37) | M = 0.71 |
| (SE = 0.42) | | (SE = 0.29) |
| Zone 7 | Zone 8 | Zone 9 |
| M = 0.79 | M = 1.43 (SE = 0.34) | M = 1.07 |
| (SE = 0.26) | | (SE = 0.38) |

Enriched Environment Post-Defecation Location (Duration)

| Zone 1 | Zone 2 | Zone 3 |
|---|---|---|
| M = 2.12 | M = 6.40 | M = 1.50 |
| (SE = 1.30) | (SE = 2.820) | (SE = 1.50) |
| Zone 4 | Zone 5 | Zone 6 |
| M = 8.97 | M = 12.10 | M = 3.17 |
| (SE = 3.28) | (SE = 2.65) | (SE = 1.28) |
| Zone 7 | Zone 8 | Zone 9 |
| M = 4.46 | M = 5.52 (SE = 1.60) | M = 3.57 |
| (SE = 1.82) | | (SE = 1.84) |

Table 77 below depicts the location within the litter box when housed in the Standard Collection Environment. The frequency table shows the mean frequency cats entered each zone. The duration table shows the mean duration cats spent in each zone. The results indicate that cats were moving throughout the litter box spending on average 23.65 to 50.95 seconds in each zone in the Standard Collection Environment.

TABLE 77

Standard Collection Environment Post-Defecation Location (Frequency)

| Zone 1 | Zone 2 |
|---|---|
| M = 8.50 (SE = 3.25) | M = 6.90 (SE = 1.26) |
| Zone 3 | Zone 4 |
| M = 9.50 (SE = 4.22) | M = 7.40 (SE = 2.42) |

Standard Collection Environment Post-Defecation Location (Duration)

| Zone 1 | Zone 2 |
|---|---|
| M = 50.95 | M = 23.65 |
| (SE = 21.63) | (SE = 6.57) |
| Zone 3 | Zone 4 |
| M = 38.98 | M = 36.63 |
| (SE = 19.24) | (SE = 18.43) |

Post-Defecation Summary

Listed below are the behavioral differences found between the two environments.

When in the Standard Collection Environment, cats stood for a longer duration (226 sec vs. 53 sec).

When in the Standard Collection Environment, cats sat for a longer duration (10 sec vs. 0 sec).

When in the Standard Collection Environment, cats sniffed eliminations for a greater duration (51 sec vs. 10 sec).

When in the Standard Collection Environment, cats pawed more often (vs. 0) and for a greater duration (78 sec vs. 1 sec).

When in the Standard Collection Environment cats had zero paws in the box more frequently (2 vs. 0) and for a greater duration (69 sec vs. 12 sec).

When in the Standard Collection Environment, cats had one paw in the box more frequently (3 vs. 1), and for a greater duration (22 sec vs. 1 sec).

Figure 7:
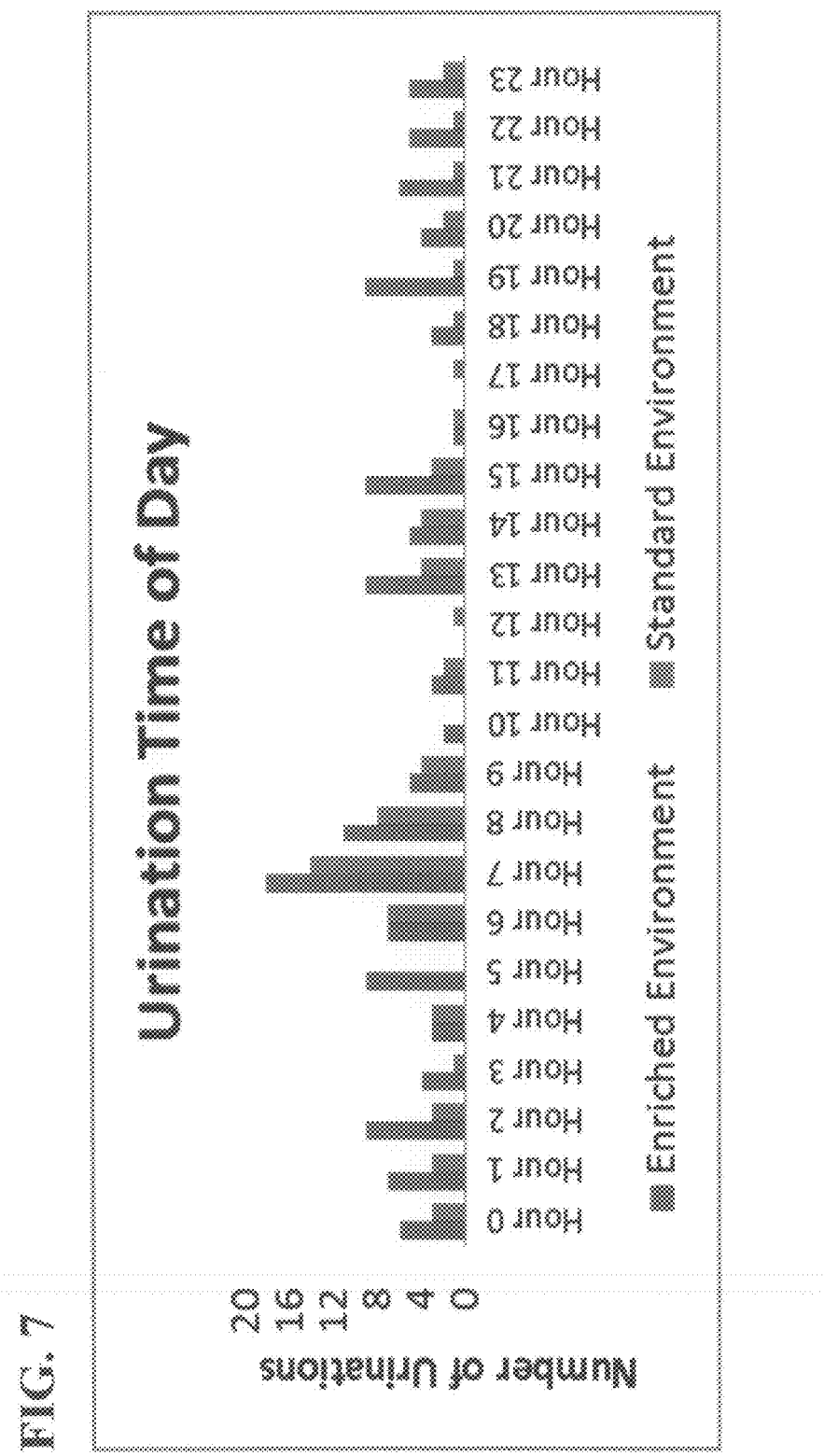

The time of day elimination events occurred was recorded on a 24 hour clock (0 to 23 hour). FIG. 7 shows the pattern of urination events throughout the day. No differences between environments were found. In both environments, cats had a peak in urinations between 7:00 am and 8:00 am.

Figure 8:
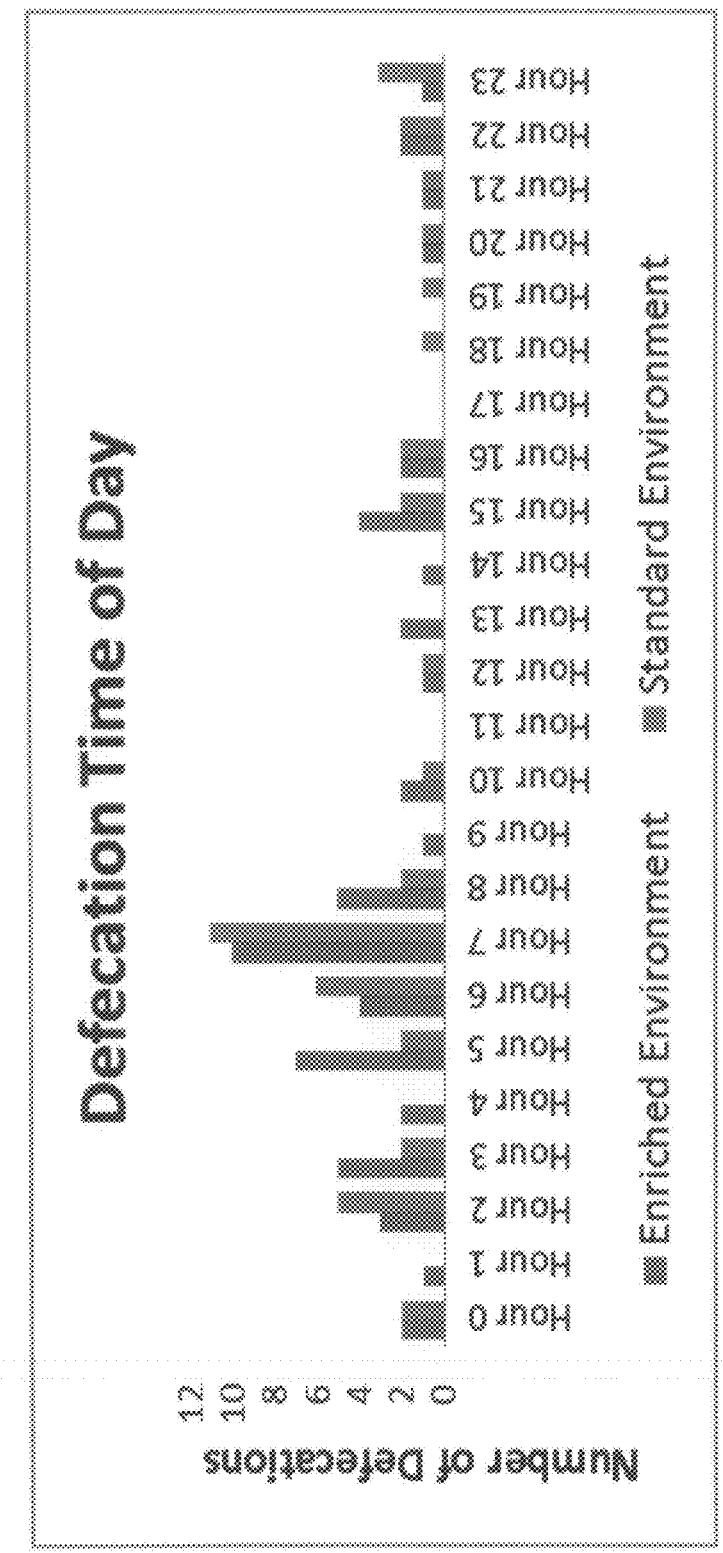

FIG. 8 shows the pattern of defecation events throughout the day. No differences between environments were found. In both environments, cats had a peak in defecations between 7:00 am and 8:00 am.

Urination Site

Table 78 below illustrates the frequency of urinations within the nine box zones in the Enriched Environment. This table shows that cats urinated in all box zones.

TABLE 78

Enriched Environment Urination Site (Frequency)

| Zone 1 | Zone 2 | Zone 3 |
|---|---|---|
| M = 0.18 | M = 0.13 | M = 0.15 |
| (SE = 0.06) | (SE = 0.05) | (SE = 0.06) |
| Zone 4 | Zone 5 | Zone 6 |
| M = 0.25 | M = 0.05 | M = 0.08 |
| (SE = 0.03) | (SE = 0.03) | (SE = 0.04) |
| Zone 7 | Zone 8 | Zone 9 |
| M = 0.15 | M = 0.13 | M = 0.10 |
| (SE = 0.06) | (SE = 0.05) | (SE = 0.05) |

Table 79 below illustrates the frequency of urinations within the four box zones in the Standard Collection Environment. The results given below indicate that cats urinated in all box zones.

TABLE 79

Standard Collection
Environment Urination
Site Location
(Frequency)

| Zone 1 | Zone 2 |
|---|---|
| M = 0.17 | M = 0.17 |
| (SE = 0.09) | (SE = 0.09) |
| Zone 3 | Zone 4 |
| M = 0.28 | M = 0.22 |
| (SE = 0.11) | (SE = 0.10) |

Defecation Site

Table 80 below depicts the defecation site frequency within the nine box zones in the Enriched Environment. The results given below indicate cats defecated in six of the nine box zones.

TABLE 80

Enriched Environment Defecation
Site Location (Frequency)

| Zone 1 | Zone 2 | Zone 3 |
|---|---|---|
| M = 0 | M = 0.10 | M = 0 |
| (SE = 0) | (SE = 0.10) | (SE = 0) |
| Zone 4 | Zone 5 | Zone 6 |
| M = 0.29 | M = 0.14 | M = 0.14 |
| (SE = 013) | (SE = 0.10) | (SE = 0.10) |
| Zone 7 | Zone 8 | Zone 9 |
| M = 0 | M = 0.07 | M = 0.21 |
| (SE = 0) | (SE = 0.07) | (SE = 0.11) |

Table 81 below illustrates the defecation site frequency when in the Standard Collection Environment. This figure shows cats defecated in three of the four box zones.

TABLE 81

Standard Collection
Environment Defecation
Site Location
(Frequency)

| Zone 1 | Zone 2 |
|---|---|
| M = 0 | M = 0.40 |
| (SE = 0) | (SE = 0.16) |
| Zone 3 | Zone 4 |
| M = 0.40 | M = 0.20 |
| (SE = 0.16) | (SE = 0.13) |

Outside of Box Events

During the eight days cats were housed in the Enriched Environment, no out of box elimination events were recorded. During the four days cats were housed in the Standard Collection Environment, four out of box urinations and five out of box defecations were recorded.

Conclusions

A catalogue of behaviors (ethogram) surrounding cat elimination was created. Before this project, very little was known about the domestic cat's natural elimination behavior. Few behaviors were previously described, such as digging, eliminating and covering. This study indicates that domestic cat elimination behavior is complex and includes as many as 39 behaviors, postures and stances.

Twelve cats were observed eliminating in two different environments. The first environment, "Enriched," consisted of a large space, moisture absorbing fine grained litter, odor coverage, and offered the ability to conceal eliminations. The second environment, "Standard Collection," consisted of a reduced space, did not provide moisture absorbency or odor coverage, and did not offer the ability to conceal eliminations.

Ninety-one eliminations (58 urinations, 24 defecations, and nine combo events) were behaviorally analyzed. Key behaviors associated with positive and frustrating litter box experiences were identified in the process. These behaviors add richness to studies of litter preference.

For instance, when cats were housed in the Standard Collection "frustrating" Environment, they would not readily enter the litter box to eliminate. Cats would waffle in and out of the litter box, and keeping one paw out of the box while eliminating was more common. In addition, cats appeared to be holding their urine and then urinating less often and for a longer duration, with their urine stream lasting on average 52 seconds (compared to 3.3 sec in the Enriched Environment).

One of the most striking behaviors observed was that cats in the Standard Collection Environment would paw at other surfaces around the litter box. On average, the pawing would last over a minute post-defecation. The pawing may be parallel to the box-banging behavior about which cat owners with hooded boxes complain.

Many of the behavioral differences occurred in the post-elimination segment. Both the post-defecation and post-urination segments were significantly longer when the cats were in the Standard Collection Environment. After eliminating in the Standard Collection Environment, cats sniffed their urinations for nearly 30 seconds and defecations for nearly a minute. Not only does this data indicate that prolonged sniffing of eliminations is a sign of frustration, but it also shows that malodor control is important to the cat's litter box satisfaction. Cats appear to have been caught in a behavioral sequence loop (returning to the box, sniffing, and pawing other substrates) due to frustration that was difficult for them to break. This behavior could be quantified either using video methods as in this study or by development of load cells (computerized scales) to automatically capture information, such as eliminations duration, frequency cat enters the box, and vibrations of the box or surrounding surfaces.

Cats will continue to use a box (and not eliminate out of the box) even when their behavior is indicative of frustration. In fact, only four out of box urinations and five out of box defecations were produced by all twelve cats over four days in the Standard Collection Environment (no out of box eliminations in the Enriched Environment). Thus, out of box elimination alone may not provide an accurate indicator of whether the cat finds the litter box experience acceptable. Out of box elimination needs to be combined with other measures of litter box use to more precisely measure the cat's acceptance.

Some behaviors may be good indicators of a positive litter box experience for cats. In the Enriched ("positive") Environment, cats readily entered and exited the box before and after eliminations. Thus a relatively brief elimination sequence is indicative of a positive experience. As noted earlier, urination was more frequent in the enriched environment. Frequent urination may be beneficial for urinary tract health and warrants further study. As with the negative behaviors identified, these positive behaviors could be quantified either using video methods as in this study or by development load cells (computerized scales) to automatically capture the information. Additional information captured may include change in weight of box after elimination is deposited and distribution of cat weight within the box over the course of an elimination event.

In the Enriched Environment, cats spent more time sniffing the litter substrate. However, in the Standard Collection Environment, the plastic beads that served as the litter substrate had little odor, which may account for why cats rarely sniffed the beads. Nevertheless, the sniffing of the granular litter in the Enriched Environment highlights the importance of malodor control and aroma appeal for cats. When designing litters, this behavioral finding should be considered. Enhancing the olfactory characteristics of litter for cats should increase cat appeal.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of evaluating litter preference, the method comprising:
   placing a first type of litter in a litter pan;
   identifying a first plurality of elimination sequences of an animal which uses the litter pan containing the first type of litter, and the identifying of the first plurality of elimination sequences is performed using at least one detection device selected from the group consisting of a motion detection device, an accelerometer, and a weighing scale;
   placing a second type of litter in a litter pan;
   identifying a second plurality of elimination sequences of an animal which uses the litter pan containing the second litter, and the identifying of the second plurality of elimination sequences is performed using the at least one detection device; and
   comparing at least one of (i) an average duration of the first plurality of elimination sequences to an average duration of the second plurality of elimination sequences or (ii) a frequency of elimination based on the first plurality of elimination sequences to a frequency of elimination based on the second plurality of elimination sequences.

2. A method of determining whether an animal is at risk of outside the box elimination, the method comprising:
   identifying a plurality of elimination sequences of an animal which uses a litter pan containing litter, the identifying performed using at least one detection device selected from the group consisting of a motion detection device, an accelerometer, and a weighing scale;
   comparing to a threshold at least one of (i) an average duration of the plurality of elimination sequences or (ii) a frequency of elimination based on the plurality of elimination sequences; and
   identifying whether the animal is at risk of outside the box elimination, the identifying based at least partially on the comparing.

3. The method of claim 1 further comprising identifying a frequency and/or a duration of an animal behavior selected from the group consisting of standing, sitting, pivoting, sniffing, pawing, placing one paw in the litter, placing three paws in the litter, exhibiting vigilance, shaking body, shaking head, wagging tail, inverting tail, and eliminating out of a litter box and combinations thereof, wherein the identifying the frequency and/or duration of an animal behavior is performed before, during or after the identifying a plurality of elimination sequences.

4. The method of claim 2 further comprising identifying a frequency and/or a duration of an animal behavior selected from the group consisting of standing, sitting, pivoting, sniffing, pawing, placing one paw in the litter, placing three paws in the litter, exhibiting vigilance, shaking body, shaking head, wagging tail, inverting tail, and eliminating out of a litter box and combinations thereof, wherein the identifying the frequency and/or duration of an animal behavior is performed before, during or after the identifying a plurality of elimination sequences.

* * * * *